(12) United States Patent
Han et al.

(10) Patent No.: US 10,451,601 B2
(45) Date of Patent: Oct. 22, 2019

(54) NANO-INDENTATION TEST TO DETERMINE MECHANICAL PROPERTIES OF RESERVOIR ROCK

(71) Applicant: Saudi Arabian Oil Company, Dhahran (SA)

(72) Inventors: Yanhui Han, Katy, TX (US); Younane N. Abousleiman, Normon, OK (US); Katherine Leigh Hull, Houston, TX (US); Ghaithan Muntasheri, Katy, TX (US)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/625,811

(22) Filed: Jun. 16, 2017

(65) Prior Publication Data

US 2017/0370895 A1 Dec. 28, 2017

Related U.S. Application Data

(60) Provisional application No. 62/355,646, filed on Jun. 28, 2016.

(51) Int. Cl.
*G01N 33/24* (2006.01)
*G01N 3/08* (2006.01)
(Continued)

(52) U.S. Cl.
CPC .............. *G01N 33/24* (2013.01); *G01N 3/08* (2013.01); *G01N 3/32* (2013.01); *G01N 3/42* (2013.01);
(Continued)

(58) Field of Classification Search
CPC ............ G01N 3/08; G01N 33/24; G01N 3/32; G01N 3/42; G01N 2203/0019;
(Continued)

(56) References Cited

U.S. PATENT DOCUMENTS

| 4,220,550 A | 9/1980 | Frenier et al. |
| 4,289,639 A | 9/1981 | Buske |

(Continued)

OTHER PUBLICATIONS

Jose et al., "Continuous multi cycle nanoindentation studies on compositionally graded TiAlN multilayer thin films," (XP028230250) Materials Science and Engineering: A, Elsevier, vol. 528, No. 21, Apr. 20, 2011; pp. 6438-6444.

(Continued)

*Primary Examiner* — Octavia Hollington
(74) *Attorney, Agent, or Firm* — Fish & Richardson P.C.

(57) ABSTRACT

Nano-indentation test to determine mechanical properties of reservoir rock can be implemented as multi-stage or single-stage tests. An experimental nano-indentation test (multi-stage or single-stage) is performed on a solid sample. A numerical nano-indentation test (multi-stage or single-stage) is performed on a numerical model of the solid sample. One or more experimental force-displacement curves obtained in response to performing the experimental nano-indentation test and one or more numerical force-displacement curves obtained in response to performing the numerical test are compared. Multiple mechanical properties of the solid sample are determined based on a result of the comparing.

16 Claims, 20 Drawing Sheets

(51) Int. Cl.
G01N 3/32 (2006.01)
G01N 3/42 (2006.01)
E21B 49/02 (2006.01)
(52) U.S. Cl.
CPC ...... E21B 49/02 (2013.01); G01N 2203/0019 (2013.01); G01N 2203/0216 (2013.01); G01N 2203/0218 (2013.01); G01N 2203/0286 (2013.01)
(58) Field of Classification Search
CPC ... G01N 2203/0216; G01N 2203/0218; G01N 2203/0286; E21B 49/005; E21B 49/02
USPC .......................................................... 73/790
See application file for complete search history.

(56) References Cited

U.S. PATENT DOCUMENTS

| | | | |
|---|---|---|---|
| 4,381,950 A | 5/1983 | Lawson | |
| 5,999,887 A | 12/1999 | Giannakopoulos et al. | |
| 6,866,048 B2 | 3/2005 | Mattox | |
| 7,621,173 B2 * | 11/2009 | Hsu | G01N 3/42 73/81 |
| 7,654,159 B2 * | 2/2010 | Enoksson | G01Q 30/02 73/862.68 |
| 8,380,437 B2 | 2/2013 | Abousleiman et al. | |
| 8,844,366 B2 * | 9/2014 | Warren | G01Q 60/366 73/780 |
| 9,753,016 B1 * | 9/2017 | Daugela | G01N 29/24 |
| 9,869,649 B2 * | 1/2018 | Hull | G01N 23/20025 |
| 9,885,691 B1 * | 2/2018 | Daugela | G01Q 60/366 |
| 2009/0193881 A1 | 8/2009 | Finnberg | |
| 2010/0186520 A1 | 7/2010 | Wheeler | |
| 2010/0213579 A1 | 8/2010 | Henry | |
| 2010/0279136 A1 | 11/2010 | Bonucci | |
| 2014/0048694 A1 | 2/2014 | Pomerantz | |
| 2015/0293256 A1 | 10/2015 | Dusterhoft | |
| 2017/0067836 A1 | 3/2017 | Hull et al. | |

OTHER PUBLICATIONS

Mahabadi et al., "A novel approach for micro-scale characterization and modeling of geomaterials incorporating actual material heterogeneity," (XP002689941) Geophysical Research Letters, American Geophysical Union, vol. 39, No. 1, L01303, Jan. 1, 2012; pp. 1-6.
International Search Report and Written Opinion issued in International Application No. PCT/US2017/038448 dated Aug. 22, 2017; 17 pages.
Goodman, "Introduction to Rock Mechanics," John Wiley & Sons, Chapter 3: Rock Strength and Failure Criteria; pp. 55-95.
Mahmoud et al., "Removal of Pyrite and Different Types of Iron Sulfide Scales in Oil and Gas Wells without H2S Generation," (IPTC-18279-MS) Presented at the International Petroleum Technology Conference (IPTC), Doha, Qatar, Dec. 6-9, 2015; 8 pages.
Wang et al., "Iron Sulfide Scale Dissolvers: How Effective Are They?" Presented at the SPE Saudi Arabia section Annual Technical Symposium and Exhibition (SPE-168063-MS), Khobar, Saudi Arabia, May 19-22, 2013; 22 pages.
Liu, "Microcantilever Testing to Evaluate the Mechanical Properties of Thermal Barrier Coatings," 19th European Conference on Fracture (ECF19): Fracture Mechanics for Durability, Reliability and Safety; Conference Proceedings held Aug. 26-31, 2012, Kazan, Russia; 7 pages.
Liu, "Dimension effect on mechanical behavior of silicon microcantilever beams," Measurement, vol. 41, No. 8, Oct. 2008; pp. 885-895.
Iqbal et al., "In situ microcantilever tests to study fracture properties of NiAl single crystals," Acta Materialia, vol. 60, No. 3, Feb. 2012; pp. 1193-1200.

Wilson et al., "Fracture testing of bulk silicon microcantilever beams subjected to a side load," Journal of Microelectromechanical Systems, vol. 5, No. 3, Sep. 1996; pp. 142-150.
Wurster et al., "Characterization of the fracture toughness of microsized tungsten single crystal notched specimens," Philosophical Magazine, vol. 92, No. 14, May 2012; pp. 1803-1825.
Abad et al., "Evaluation of the Material Properties of the Multilayered Oxides formed on HCM12A using New and Novel Techniques," Manuscript Draft, Manuscript No. OXID-D-15-00019, published in 2015, 44 pages.
Abousleiman et al, "A Micromechanically Consistent Poroviscoelasticity Theory for Rock Mechanics Applications," Int. J. Rock Mech. Min. Sci. & Geomech. Abstr., vol. 30, No. 7, published in 1993, pp. 1177-1180.
Abousleiman et al, "Anisotropic Porothermoelastic Solution and Hydro-Thermal Effects on Fracture Width in Hydraulic Fracturing," Int. J. Numer. Anal. Meth. Geomech., published in 2013, 25 pages.
Abousleiman et al, "Geomechanics Field and Laboratory Characterization of Woodford Shale: The Next Gas Play," SPE International, SPE 110120, Copyright 2007, 14 pages.
Abousleiman et al, "Poroviscoelastic Analysis of Borehole and Cylinder Problems," ACTA Mechanica, vol. 119, published in 1996, pp. 199-219.
Abousleiman et al., "GeoGenome Industry Consortium (G2IC)," JIP, 2004-2006, 6 pages.
Abousleiman et al., "Geomechanics Field Characterization of the Two Prolific U.S. Mid-West Gas Plays with Advanced Wire-Line Logging Tools," SPE International, SPE 124428, Copyright 2009, 19 pages.
Abousleiman et al., "Mandel's Problem Revisited," Geotechnique, 46, No. 2, published in 1996, pp. 187-195.
Abousleiman et al., "Mechanical Characterization of Small Shale Samples subjected to Fluid Exposure using the Inclined Direct Shear Testing Device," Int. J. Rock Mech. & Min. Sci., vol. 47, No. 3, published in 2010, pp. 355-367.
Abousleiman et al., "Poroelastic Solutions in Transversely Isotropic Media for Wellbore and Cylinder," Int. J. Solids Structures, vol. 35, Nos. 34-35, published in 1998, pp. 4905-4929.
Abousleiman et al., "The Granular and Polymer Composite Nature of Kerogen-Rich Shale," Acta Geotechnica, Feb. 5, 2016, 24 pages.
Allan et al., "A Multiscale Methodology for the Analysis of Velocity Anisotropy in Organic-Rich Shale," Geophysics, vol. 80, No. 4, Jul.-Aug. 2015, 16 pages.
Ananthan et al., "Influence of Strain Softening on the Fracture of Plain Concrete Beams," Int. J. of Fracture, vol. 45, published in 1990, pp. 195-219.
Ballice, "Solvent Swelling Studies of Goynuk (Kerogen Type-I) and Beypazari Oil Shales (Kerogen Type-II)," Science Direct, published in 2003, pp. 1317-1321.
Bazant et al., "Deformation of Progressively Cracking Reinforced Concrete Beams," ACI Journal, Technical Paper, Title No. 81-26, vol. 81, No. 3, May-Jun. 1984, pp. 268-278.
Bazant et al., "Strain-Softening Bar and Beam: Exact Non-Local Solution," Int. J. Solids Structures, vol. 24, No. 7, published in 1988, pp. 659-673.
Bennett et al., "Instrumented Nanoindentation and 3D Mechanistic Modeling of a Shale at Multiple Scales," Acta Geotechnica, published in 2015, 14 pages.
Bhandari et al., Two-Dimensional DEM Analysis of Behavior of Geogrid-Reinforced Uniform Granular Bases under a Vertical Cyclic Load, Acta Geotechnica, published in 2014, pp. 469-480.
Biot, "General Theory of Three-Dimensional Consolidation," Journal of Applied Physics, vol. 12, No. 2, Feb. 1941, pp. 155-164.
Bobko et al., "The Nanogranular Origin of Friction and Cohesion in Shale—A Strength Homogenization Approach to Interpretation of Nanoindentation Results," Int. J. Numer. Anal. Meth. Geomech., published in 2010, 23 pages.
Boskey et al., "Perspective—Collagen and Bone Strength," Journal of Bone and Mineral Research, vol. 14, No. 3, published in 1999, 6 pages.
Chen et al., "Size Effect in Micro-Scale Cantilever Beam Bending," Acta Mech., published in 2011, pp. 291-307.

(56) References Cited

OTHER PUBLICATIONS

Chern et al., "Deformation of Progressively Cracking Partially Prestressed Concrete Beams," PCI Journal, vol. 37, No. 1, published in 1992, pp. 74-84.

Chupin et al., "Finite Strain Analysis of Nonuniform Deformation Inside Shear Bands in Sands," Int. J. Numer. Anal. Meth. Geomech., published in 2012, pp. 1651-1666.

Deirieh et al., "Nanochemomechanical Assessment of Shale: A Coupled WDS-Indentation Analysis," Acta Geotechnica, published in 2012, 25 pages.

Ekbote et al., "Porochemoelastic Solution for an Inclided Borehole in a Transversely Isotropic Formation," J. of Eng. Mech., ASCE, Jul. 2006, 10 pages.

Ertas et al., "Petroleum Expulsion Part 1. Theory of Kerogen Swelling in Multicomponent Solvents," Energy & Fuels, published in 2006, pp. 295-300.

Ewy, "Shale Swelling/Shrinkage and Water Content Change due to Imposed Suction and Due to Direct Brine Contact," Acta Geotechnica, published in 2014, pp. 869-886.

Frazer et al., "Localized Mechanical Property Assessment of SiC/SiC Composit Materials," Science Direct, Part A 70, published in 2015, pp. 93-101.

Gao et al., "Materials Become Insensitive to Flaws at Nanoscale: Lessons from Nature," PNAS, vol. 100, No. 10, May 13, 2003, pp. 5597-5600.

Garnero, "The Contribution of Collagen Crosslinks to Bone Strength," Int. Bone & Mineral Society, Sep. 2012, 8 pages.

Han et al., "LBM-DEM Modeling of Fluid-Solid Interaction in Porous Media," Int. J. Numer. Anal. Meth. Geomech., published in 2013, pp. 1391-1407.

Hoang et al., "Correspondence Principle Between Anisotropic Poroviscoelasticity and Poroelasticity using Micromechanics and Application to Compression of Orthotropic Rectangular Strips," Journal of Applied Physics, American Institute of Physics, vol. 112, Aug. 30, 2012, 16 pages.

Hornby et al., "Anisotropic Effective-Medium Modeling of the Elastic Properties of Shales," Geophysics, vol. 59, No. 10, Oct. 1994, pp. 1570-1583.

Hosemann et al, "Mechanical Characteristics of SiC Coating Layer in TRISO Fuel Particles," Journal of Nuclear Materials, vol. 442, published in 2013, pp. 133-142.

Hosemann et al., "An Exploratory Study to Determine Applicability of Nano-Hardness and Micro-compression Measurments for Yield Stress Estimation," Science Direct, published in 2008, pp. 135-143.

Iyengar et al., "Analysis of Crack Propagation in Strain-Softening Beams," Engineering Fracture Mechanics, published in 2002, pp. 761-778.

Kelemen et al., "Petroleum Expulsion Part 2. Organic Matter Type and Maturity Effects on Kerogen Swelling by Solvents and Thermodynamic Parameters for Kerogen from Regular Solution Theory," Energy & Fuels, published in 2006, pp. 301-308.

Kolymbas, "Kinematics of Shear Bands," Acta Geotechnica, published in 2009, pp. 315-318.

Lam et al., "Experiments and Theory in Strain Gradient Elasticity," J. Mech. And Phys. Of Solids, published in 2003, pp. 1477-1508.

Larsen et al., "Changes in the Cross-Link Density of Paris Basin Toarcian Kerogen During Maturation," Organic Geochemistry, published in 2002, pp. 1143-1152.

Li et al., "Mechanical Characterization of Micro-Nanoscale Structures for MEMS/NEMS Applications using Nanoindentation Techniques," Science Direct, published in 2003, pp. 481-494.

Maio et al., "Measuring Fracture Toughness of Coatings using Focused-ion-beam-machined Microbeams," published in 2004, 4 pages.

Oliver, "An Improved Technique for Determining Hardness and Elastic Modulus using Load and Displacement Sensing Indentation Experiments," published in 1992, 20 pages.

Ortega et al., "The Effect of Particle Shape and Grain-Scale Properties of Shale: A Micromechanics Approach," Int. J. Numer. Anal. Methd. Geomech., published in 2010, pp. 1124-1156.

Ortega et al., "The Effect of the Nanogranular Nature of Shale on their Poroelastic Behavior," Acta Geotechnica, published in 2007, pp. 155-182.

Ortega et al., "The Nanogranular Acoustic Signature of Shale," Geophysics, vol. 74, No. 3, May-Jun. 2009, 20 pages.

Passey et al., "From Oil-Prone Source Rock to Gas-Producing Shale Reservoir—Geologic and Petrophysical Characterization of Unconventional Shale-Gas Reservoirs," Society of Petroleum Engineers International, CPS/SPE International Oil & Gas Conference and Exhibition, Beijing, China, Jun. 8-10, 2010, 29 pages.

Podio et al., "Dynamic Properties of Dry and Water-Saturated Green River Shale under Stress," Jun. 11, 1968, SPE 1825, 16 pages.

Richard et al, "Slow Relaxation and Compaction of Granular Systems," Nature Materials, vol. 4, Feb. 2005, 8 pages.

Shin et al., "Development and Testing of Microcompression for Post Irradiation Characterization of ODS Steels," J. Nuclear Materials, published in 2014, pp. 43-48.

Sierra et al., "Woodford Shale Mechanical Properties and the Impacts of Lithofacies," ARMA 10-461, copyright 2010, 10 pages.

Slatt et al., "Merging Sequence Stratigraphy and Geomechanics for Unconventional Gas Shales," The Leading Edge, Mar. 2011, 8 pages.

Slatt et al., Outcrop/Behind Outcrop (Quarry), Multiscale Characterization of the Woodford Gas Shale, copyright 2011, 22 pages.

Sone et al., "Mechanical Properties of Shale-Gas Reservoir Rocks—Part 1: Static and Dynamic Elastic Properties and Anisotropy," Geophysics, vol. 78, No. 5, Sep.-Oct. 2013, pp. D381-D392.

Ulm et al., "Material Invariant Poromechanics Properties of Shales," published in 2005, pp. 637-644.

Ulm et al., "The Nanogranular Nature of Shale," Acta Geotechnica, published in 2006, 12 pages.

Vernik et al., "Ultrasonic Velocity and Anisotropy of Hydrocarbon Source Rocks," Geophysics, vol. 57, No. 5, May 1992, pp. 727-735.

Wenk et al., "Preferred Orientation and Elastic Anisotropy of Illite-Rich Shale," Geophysics, vol. 72, No. 2, Mar.-Apr. 2007, pp. E69-E75.

Zeszotarski et al., "Imaging and Mechanical Property Measurements of Kerogen via Nanoindentation," Geochimica et Cosmochimica Acta, vol. 68, No. 20, published in 2004, pp. 4113-4119.

Georgl et al., "Physics and Chemistry in Nanoscale Rocks", Mar. 22-26, 2015, La Jolla, California, USA, SPE Forum Series 4 pages.

Sone et al., "Mechanical properties of shale-gas reservoir rocks—Part 2: Ductile creep, brittle strength, and their relation to the elastic modulus," 2013, Geophysics, vol. 78, No. 5, pp. D393-D402.

Vanlandingham, "Review of Instrumented Indentation," Journal of Research of the National Institute of Standards and Technology, vol. 108, No. 4, Jul.-Aug. 2003, 17 pages.

Poon et al., "An Analysis of Nanoindentation in Linearly Elastic Solids," International Journal of Solids and Structures, published in 2008, 16 pages.

Wang et al., "A Numerical Study of Factors Affecting the Characterization of Nanoindentation on Silicon," Materials Science and Engineering, Published in 2007, pp. 244-253.

Eliyahu et al., "Mechanical Properties of organic matter in shales mapped at the nanometer scale," Marine and Petroleum Geology, vol. 59, Jan. 2015, 11 pages.

Eseme et al., "Review of mechanical properties of oil shales: implications for exploitation and basin modeling," Oil Shale, vol. 24, No. 2, Jan. 2007, 16 pages.

Rodriguez et al., "Imagining techniques for analyzing shale pores and minerals," National Energy Technology Laboratory, Dec. 2, 2014, 44 pages.

Gulf Cooperation Council Examination Report issued in GCC Application No. GC 2016-31981 dated Sep. 24, 2018, 4 pages.

\* cited by examiner

NANO-INDENTATION TEST TO DETERMINE MECHANICAL PROPERTIES OF RESERVOIR ROCK

CROSS REFERENCE TO RELATED APPLICATION(S)

This application claims the benefit of priority to U.S. Provisional Patent Application Ser. No. 62/355,646, filed Jun. 28, 2016, the contents of which are hereby incorporated by reference.

TECHNICAL FIELD

This disclosure relates to determining mechanical properties of materials, for example, heterogeneous materials such as reservoir rock.

BACKGROUND

Hydrocarbon production involves retrieving hydrocarbons trapped inside rocks in hydrocarbon reservoirs. In some situations, the hydrocarbon reservoirs can be fractured, for example, by hydraulic fracturing, to allow the trapped hydrocarbons to flow to wells drilled in the reservoir. Knowledge of mechanical properties of the reservoir rock is required in hydraulic fracturing design. One method to obtain the mechanical properties of the reservoir rock is to obtain samples of the rock from the reservoir and to test the samples, for example, in a laboratory.

SUMMARY

This specification describes technologies relating to nano-indentation test to determine mechanical properties of reservoir rock.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
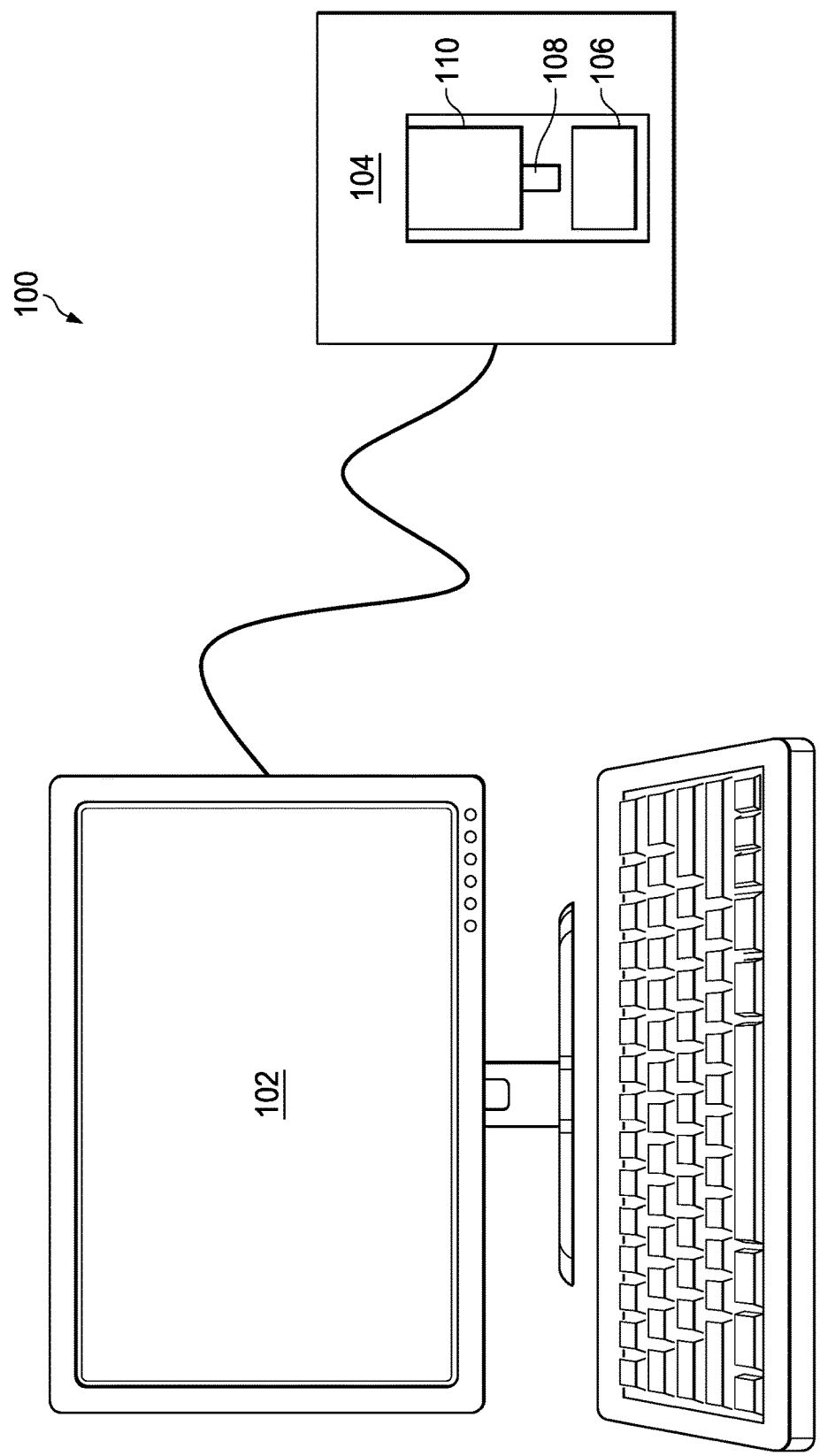
FIG. 1 shows a schematic of an example of a nano-indentation test system.

To effectively and efficiently produce hydrocarbons that are stored in the underground rocks, it is important to understand the mechanical properties and behaviors of the reservoir rocks and the overburdens in the oil and gas exploration and production engineering activities. For example, in order to maintain the stability of the borehole during drilling, an appropriate mud weight should be selected such that both borehole breakout and borehole fracturing are prevented. In addition to the in situ stress field, the cohesive strength and frictional angle are primary mechanical properties in the borehole breakout while tensile strength is relevant in borehole fracturing.

Shales are the most common sedimentary rocks, that is, around half of sedimentary rocks on earth are shales. For conventional reservoirs, most overburden and seal rocks are shales. For unconventional reservoirs, shales are also the source rocks in addition to serving as overburden and seal layers. Understanding of mechanical properties and behaviors of shales are important in drilling, completion, and production for almost all oil and gas wells.

Cohesive strength and frictional angle of geological materials are indirectly measured by performing confined compression tests on cylindrical core samples in conventional lab. The tensile strength can be measured in direct tensile test, but more often using the Brazilian test in which the tensile strength is determined through crushing a rock disk. Both compression and tensile tests require inch-sized cylindrical cores or discs; this type of core is usually unavailable, especially for the overburden and seal rocks. Small rock cuttings are circulated to the ground surface with mud when drilling a well and carry all the mineralogical and mechanical information of their source rocks. It is convenient to determine properties of source rocks from these cuttings. This disclosure aims at extracting mechanical properties of the shales by performing multistage nano-indentation tests on shale sample or cuttings.

Nano-indentation is a testing technique to measure the local mechanical properties of materials at micro- and nano-scale. The majority of existing nano-indentation work has been performed on homogeneous materials, such as steel, film and coating. Typical measurements taken with this technique are the elastic modulus and one yielding strength parameter. For the interest of engineering design, elastic modulus is not sufficient, a full set of mechanical properties is required. A method of extracting cohesive strength, frictional angle and tensile strength by performing numerical modeling to fit lab data collected in multistage nano-indentation tests is disclosed. The disclosed method extracts the full set of mechanical properties, both elastic and plastic, from the force-displacement curve recorded in the nano-indentation test.

The mechanical behavior of the contact in nano-indenting geological materials, such as reservoir rock shales, is simulated using continuum mechanics approach. The nano-indenter tip and geometry are modeled as a hemispherical elastic object, and the indented blocks are modeled as Mohr-Coulomb type failure geomaterials. The deformation and slip, at micro-meter scale, along the shear direction, in grain to grain contact follows the Coulomb friction/sliding criterion, while linear elastic force-displacement law is enforced in the direction normal to the contact. A series of simulations are performed to study the effect of plastic properties of indented material, including cohesive, frictional and tensile strengths, on the micro-mechanical response in the indentation process. For very high cohesion material and smooth contact, the indented material behaves elastically. In this case, the indentation process converges to the classic Hertz grain-to-grain spherical contact problem and the force-displacement curve monitored in the numerical model is compared with the Hertz solution. For extremely low cohesion, the micro-geomaterial, behaves like cohesionless granular material. For finite cohesion values for the shale, the force-displacement responses recorded in the simulation are analyzed in details. This simulation is compared to some initial micro-indentation tests, conducted on Woodford shales.

As disclosed in this specification, lab test and numerical modeling are tightly combined to explore the possibility to extract multiple elastoplastic properties from force-displacement curve recorded in the test of indenting shale samples. Micro-material indentation equipment with a spherical indenter are used to indent shale samples. The numerical models are then built to mimic the indentation test. In the numerical model, the mechanical behavior of the contact in nano-indenting geological materials, such as reservoir rock shales, is simulated using continuum mechanics approach. The nonindenter tip and geometry are modeled as a hemispherical elastic object, and the indented blocks are Mohr-Coulomb type geomaterials. The deformation and slip, at micro-meter scale, along the shear direction, in grain to grain contact follows the Coulomb friction/sliding criterion, while linear elastic force-displacement law is enforced in the direction normal to the contact.

Several simulations are performed to study the effect of plastic properties of indented material, including cohesive, frictional and tensile strengths, on the micro-mechanical response in the indentation process. For very high cohesion material and smooth contact, the indented material behaves elastically; the indentation process converges to the classic Hertz spherical contact problem and the force-displacement curve monitored in the numerical model was compared with the Hertz solution. For materials with finite strength values, the sensitivity of force-displacement responses recorded in the simulation to material strength variation were tested and analyzed.

Experimental System Section
Nano Indentation Test System

FIG. 1 shows an example of an experimental system 100 to implement the nano-indentation test on a reservoir rock sample. This system 100 includes a nano-indenter 104 with calibrated sensors, a material sample 106 for testing, and a computer 102. The computer 102 is used to record and plot the data collected by the nano-indenter 104 and to develop a numerical model to extract mechanical properties from lab testing results. In some implementations, the numerical model can be developed using a different computer system (not shown). The nano-indenter 104 has a nano-indenter tip 108 that first touches then penetrates into the surface 110 of a material sample 106 with a specific amount of force or to a specific depth or both.

There are two types of nano-indentation tests disclosed: a single-stage test and a multi-stage test. The single-stage test involves loading the nano-indenter tip 108 to a set load on a lab sample and then releasing the load in its entirety, that is, releasing the load to zero. Alternatively, the nano-indenter tip 108 is loaded to a set displacement on a lab sample and then releasing the load in its entirety. The force-displacement curve is recorded by a computer 102 communicating with the nano-indenter machine 104, for example, during the indenting stage or the withdrawing stage or both, and the results are compared to a numerical model. The test is performed multiple times at different points on the sample surface 110. The resulting force-displacement curves are averaged together to form a single average composite curve.

In a multi-stage test, the nano-indenter tip 108 is pressed into the surface 110 of a sample 106 at a set load and released to a lesser load, for example, a non-zero load. This process is repeated for subsequently higher loads for multiple, for example three, cycles, and the force-displacement curves are recorded and compared to a numerical model. The set load and the lesser load in each cycle can be less than a corresponding set load and lesser load in a preceding cycle. The lesser load in the last cycle can be a zero load in which the nano-indenter is entirely withdrawn from the sample. Alternatively, the nano-indenter tip 108 is loaded to a first displacement on a lab sample and withdrawn to less than the first displacement (but not in its entirety). This process is repeated for subsequently higher indentation depths for multiple, for example, three cycles, and the force-displacement curves are recorded and compared to a numerical model. The indentation depth and withdrawal depth in each cycle can be less than a corresponding indentation depth and a withdrawal depth in a preceding cycle.

For both tests, the sample can be indented to a depth that is at most $\frac{1}{10}^{th}$ of a thickness of the sample. Also, material properties of the sample 106 are determined by adjusting the material properties in the numerical model until the numerical model's load-displacement curves substantially match the empirical load-displacement curves from the physical nano-indentation tests. For example, the two load-displacement curves are determined to match if a difference between the two curves is within a threshold variance (for example, between 1% and 10%) indentation. These tests can be performed on any solid material, including heterogeneous materials such as shales.

Numerical Modeling Test System

Rigorous analysis of stress at the contact between two elastic solids was first performed by Hertz. In the problem sketched in FIG. 2, a spherical object initially touches the half space at a single point. Under the action of a load, two objects deform at the contact point and the point contact develops into an area contact. If both solid objects are linear elastic materials, the relationship between the load, elastic deformation and geometric properties of two objects and movement at the sphere center (from which the penetration depth can be calculated) can be described by the following formula:

$$F = 4/3 E^* R^{1/2} \delta^{3/2} \qquad (1)$$

where F is the applied vertical load; R is the radius of the spherical indenter; δ is the vertical displacement at the center of spherical indenter; E* is an intermediate variable determined by the stiffness parameters of indenter and indented material, that is, $$\frac{1}{E^*} = \frac{(1-v_s^2)}{E_s} + \frac{(1-v_p^2)}{E_p} \qquad (2)$$

where $E_s$ and $v_s$ are Young's modulus and Poisson's ratio of the indented material; $E_p$ and $v_p$ are Young's modulus and Poisson's ratio of the indenter.

Hertz contact problem is the foundation of indentation testing technique. From the perspective of numerical modeling, a trustworthy numerical model demonstrates its capability in recovering Hertz solution before it is applied to model indentation in more complicated rheological or elastoplastic materials. An appropriate mesh resolution is required in modeling indentation tests in order to accurately capture the mechanical behavior at the contact, which can be found out by modeling Hertz contact problem.

Figure 3:
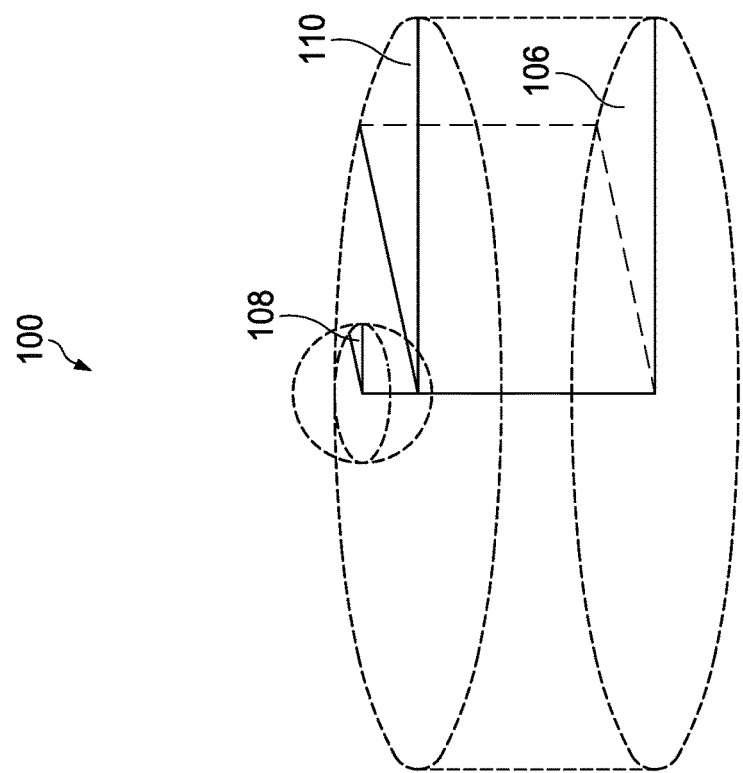
FIG. 3 demonstrates the axisymmetric nature of the Hertz contact problem.
Figure 2:
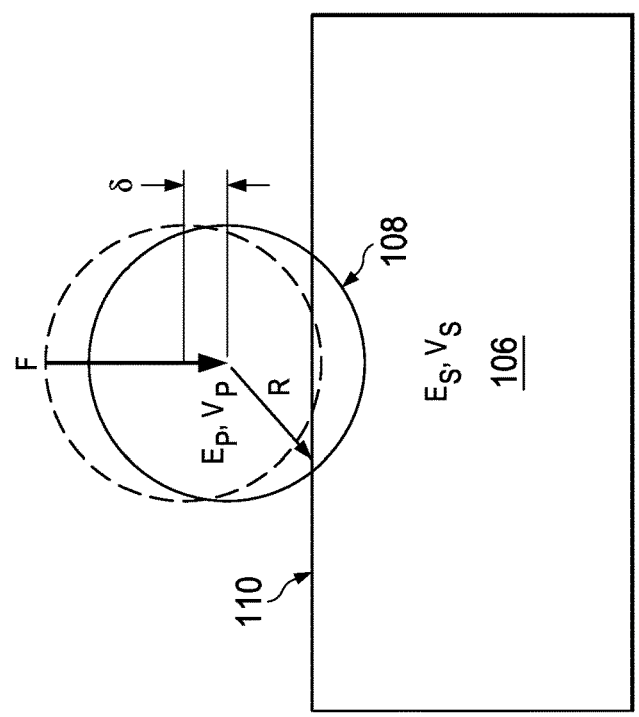
FIG. 2 shows a graphical representation of the Hertz equation.

The object of half space in FIG. 2 may be represented by a cylindrical block in FIG. 3, as long as the block size is much larger than the sphere size. The problem can be perfectly modeled in a two-dimensional, axisymmetric model due to the axisymmetric nature of this sphere-cylinder contact configuration. An example represented by two solid slices is shown in FIG. 3.

Figure 4:
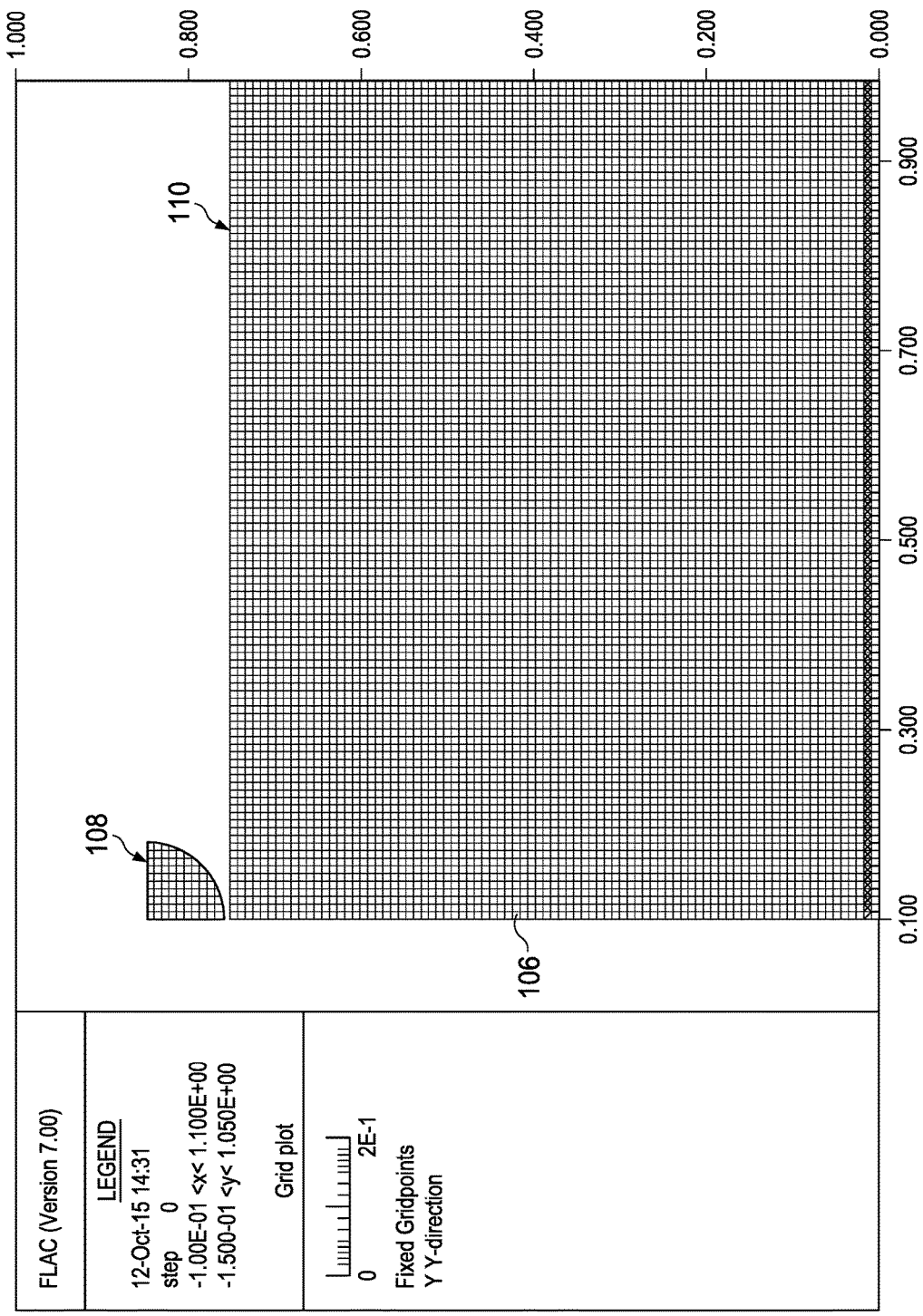
FIG. 4 shows an example of a numerical mesh used for numerical analysis approximating the Hertz contact problem.

After a few attempts from coarse to fine mesh in Fast Langrangian Analysis of Continua (FLAC), a numerical simulation software, the resolution in the mesh shown in FIG. 4 is sufficient for accurately capturing the mechanical behavior of the contact. In the example model, the cylindrical block had radius of 1 m and height of 0.8 m and the sphere had radius of 0.1 m. The element size of the block was 0.01 m and the element size of the sphere was 0.005 m. The elastic properties of spherical indenter ($E_p, v_p$) and the indented cylindrical blocks ($E_s, v_s$) were:

$E_p = 27$ GPa
$v_p = 0.35$
$E_s = 2.7$ GPa
$v_s = 0.35$

In real indentation testing, the indenter is typically much stiffer than the indented materials. A much lower stiffness is intentionally assigned to the indenter to examine the capability of the numerical model in capturing contact mechanics in general, as the effect of the indenter stiffness is suppressed when it is much higher than that of indented material, as indicated by Eq. (2). The contact between the spherical indenter and the indented cylinder is smooth. Its stiffness properties were estimated from element properties following the recommendation in FLAC user manual, that is, 20 times the confined modulus of the elements divided by the smallest size of the elements along the contact.

Figure 5:
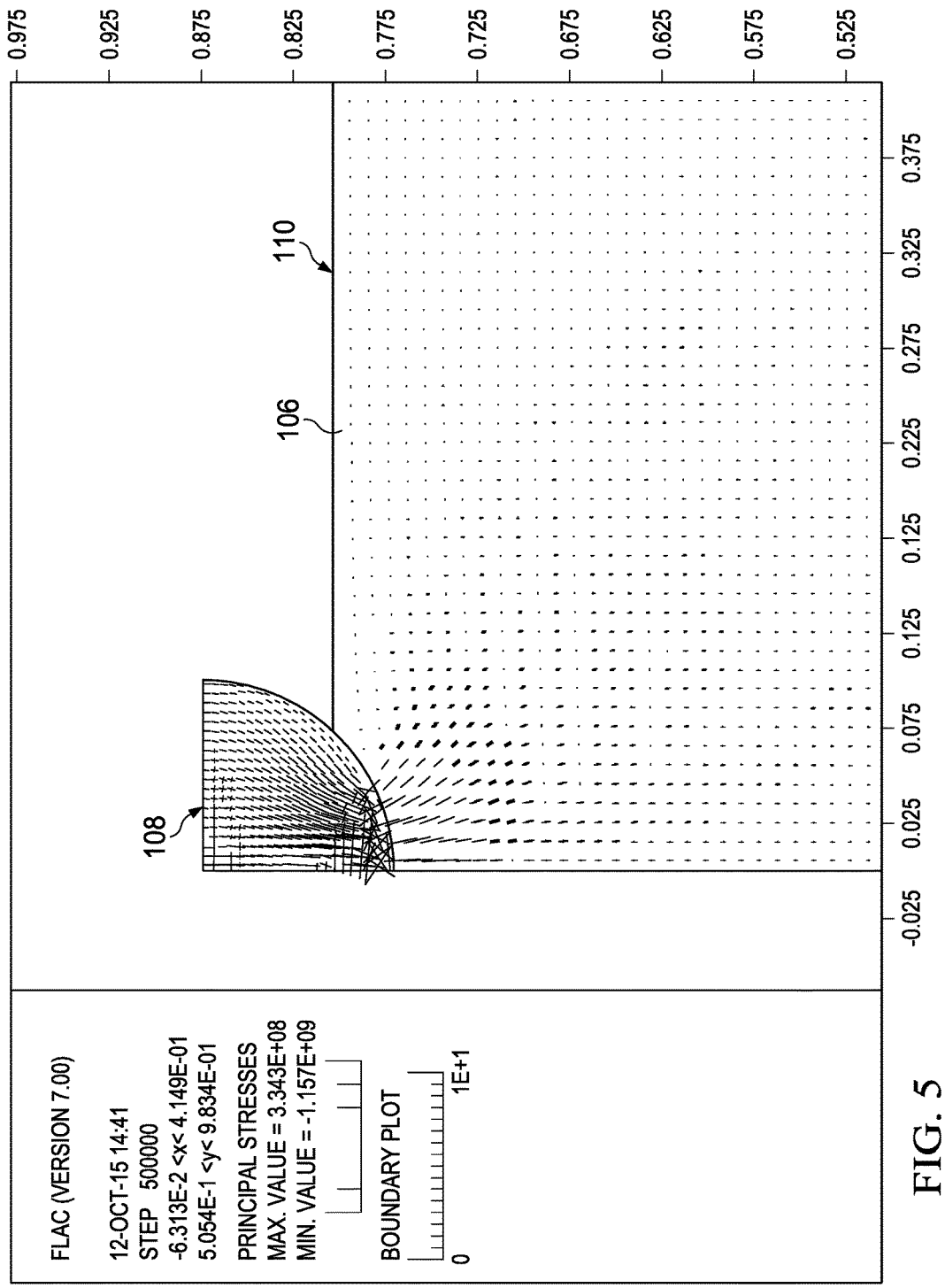
FIG. 5 shows an example of the deformed mesh resulting from a numerical analysis.
Figure 6:
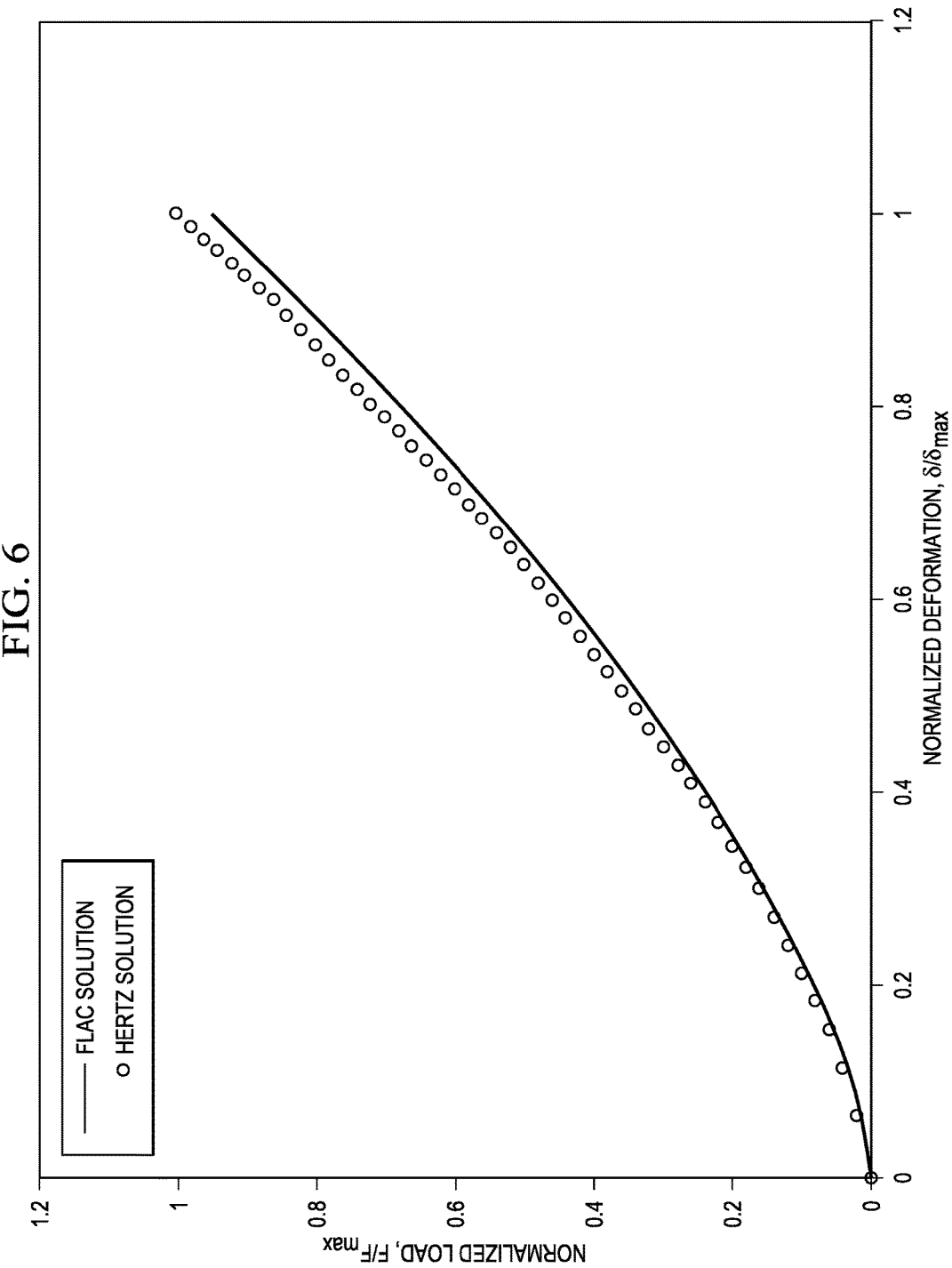
FIG. 6 shows the similarity of the numerical model solution to the solution of Hertz problem.

The indented block has roller boundary at the bottom (see FIG. 4). Initially the indenter touches the indented block at a single point. The indentation was driven by a pressure, which is increased from zero to 5000 KN over 500 thousand steps at the top surface of the indenter. During the simulation, the applied load at the indenter's top surface and the displacement at the center of the indenter is recorded and used to calculate the applied load from analytical solution in Eq. (1). FIG. 5 displays the deformed mesh induced by indentation and principal stress vectors at the end of the simulation. An example force-displacement curve recorded in the numerical model is compared with analytical prediction in FIG. 6, in which the load is normalized by 5000 KN and the displacement is normalized by the maximum displacement, 2.5 cm, reported by the numerical model. When the deformation is small, the errors between the numerical and analytical solutions are around 1%. The error increases as deformation increases, for instance, the error reaches 7% at the end of the simulation where the deformation is 2.5 cm. This is consistent with the assumption of Hertz contact solution, that is, the indentation depth should be small in relation to the indenter size.

The material in the indented block for this simulation was switched to Mohr-Coulomb type elastoplastic materials and indentation test is repeated for various combinations of plastic properties, experimenting how mechanical properties affect the force-displacement curve recorded in the indentation test. Mohr-Coulomb type material can yield in both compressive and tensile modes. Under compressive loading mode, the material can yield in shear and the shear yielding criterion is described by:

$$\sigma_1 = \frac{1+\sin\varphi}{1-\sin\varphi}\sigma_3 + \frac{2\cos\varphi}{1-\sin\varphi}c \qquad (3)$$

where $\sigma_1$ and $\sigma_3$ are the maximum and minimum compressive principal stress, respectively; C is the cohesive strength and φ is the internal frictional angle. Compressive shear yielding is determined by cohesive strength, frictional angle, and confining stress. In the tensile loading mode, brittle failure occurs instantaneously when the tensile strength exceeds the tensile strength.

Some variants of Mohr-Coulomb model can describe more complicated mechanical behaviors of geological materials, such as in strain-softening model. All the strength parameters can be specified as functions of plastic strains, which are derived by matching full stress-strain curves recorded in the servo-control type laboratory experiments. The ductile tensile yielding and softening/hardening shear yielding can be modeled using these advanced constitutive models. The numerical modeling disclosed below is limited to the basic Mohr-Coulomb material model.

In the parametric sensitivity study below, the effects of each individual plastic property (i.e., cohesive strength, frictional angle and tensile strength) on the force-displacement curves are explained separately in the following paragraphs. In all the tests the load is increased to the maximum load over, 200 thousand steps, held at the peak load, 20 thousand steps and then decreased to zero over, 200 thousand steps.

Figure 7A:
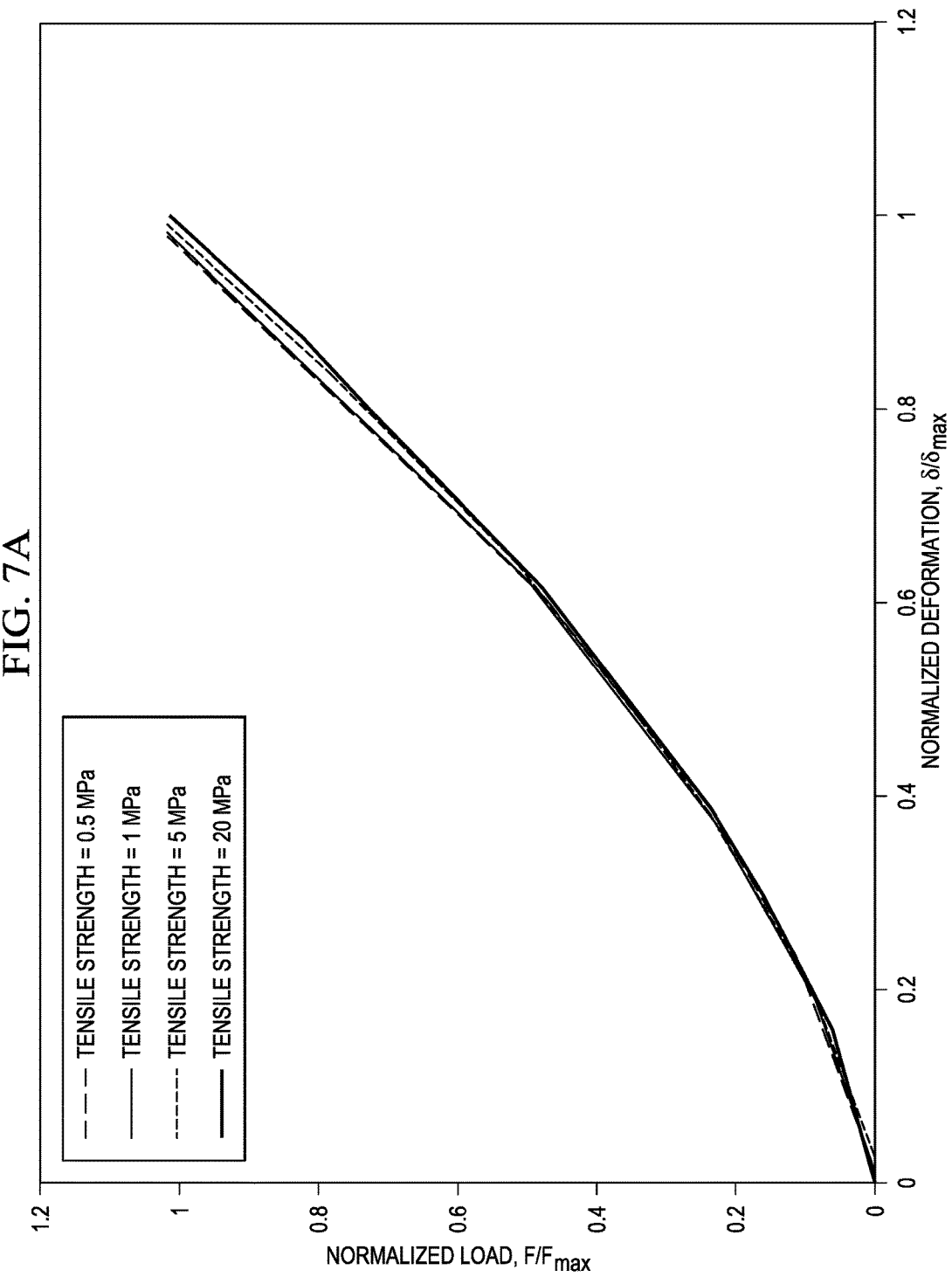
FIG. 7A shows the effect of adjusting tensile strength on the force-displacement curves in the numerical model.
Figure 7B:
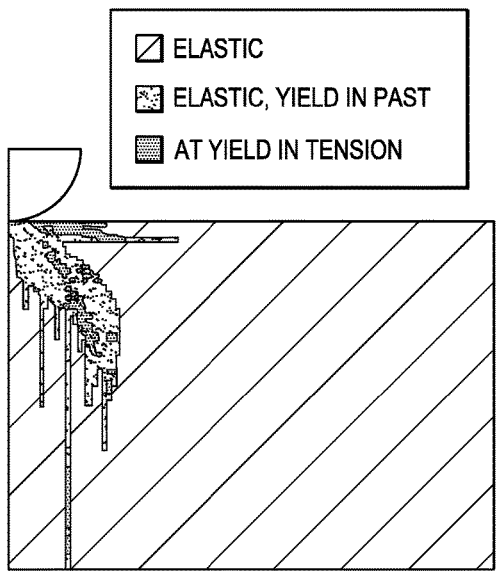
FIGS. 7B-7E shows the extensions and shapes of plastic region at the end of a numerical simulation adjusting tensile strength.
Figure 7C:
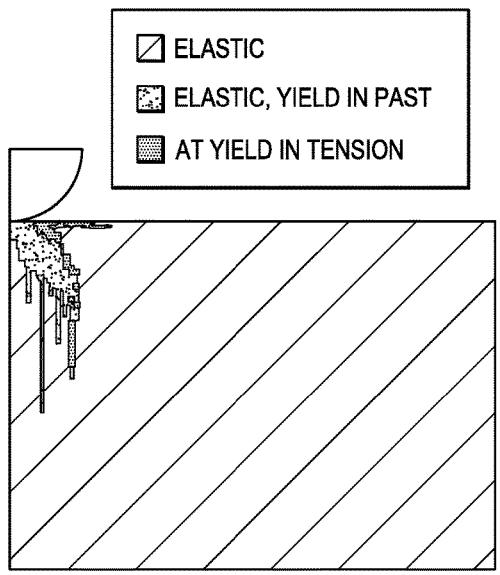
Figure 7D:
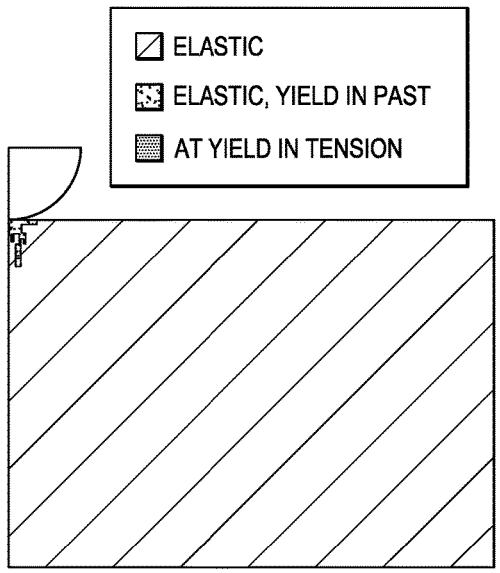
Figure 7E:
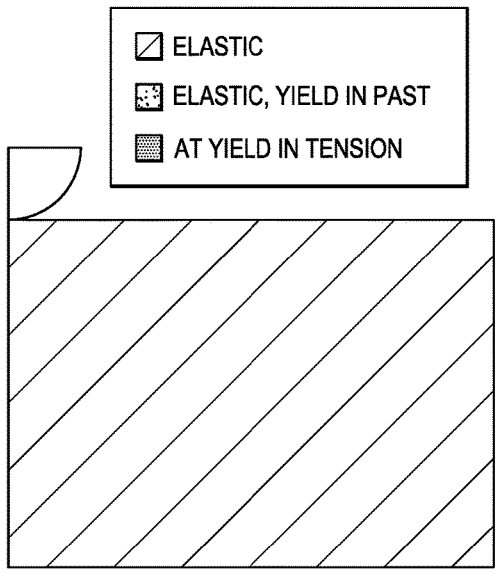

To observe how tensile strength affects the force-displacement curves in the indentation tests, an indentation simulation was repeated for the simulated sample's tensile strengths of 0.5, 1, 5 and 20 MPa. The influence of cohesive strength was excluded by setting it to a high value to completely prevent shear yielding. All these simulations stopped at the same maximum load (500 KN). The monitored force-displacement curves are presented in FIG. 7A. The plastic regions at the end of the simulations are provided in FIGS. 7B-7E. As can be seen, there is no tensile yielding with tensile strength of 20 MPa, whereas the tensile yielding is quite extensive in the case of 0.5 MPa tensile strength. However, there is no significant difference in the recorded force-displacement curves in all these cases. It seems that tensile strength has relatively trivial effect on the force-deformation curve.

Figure 8A:
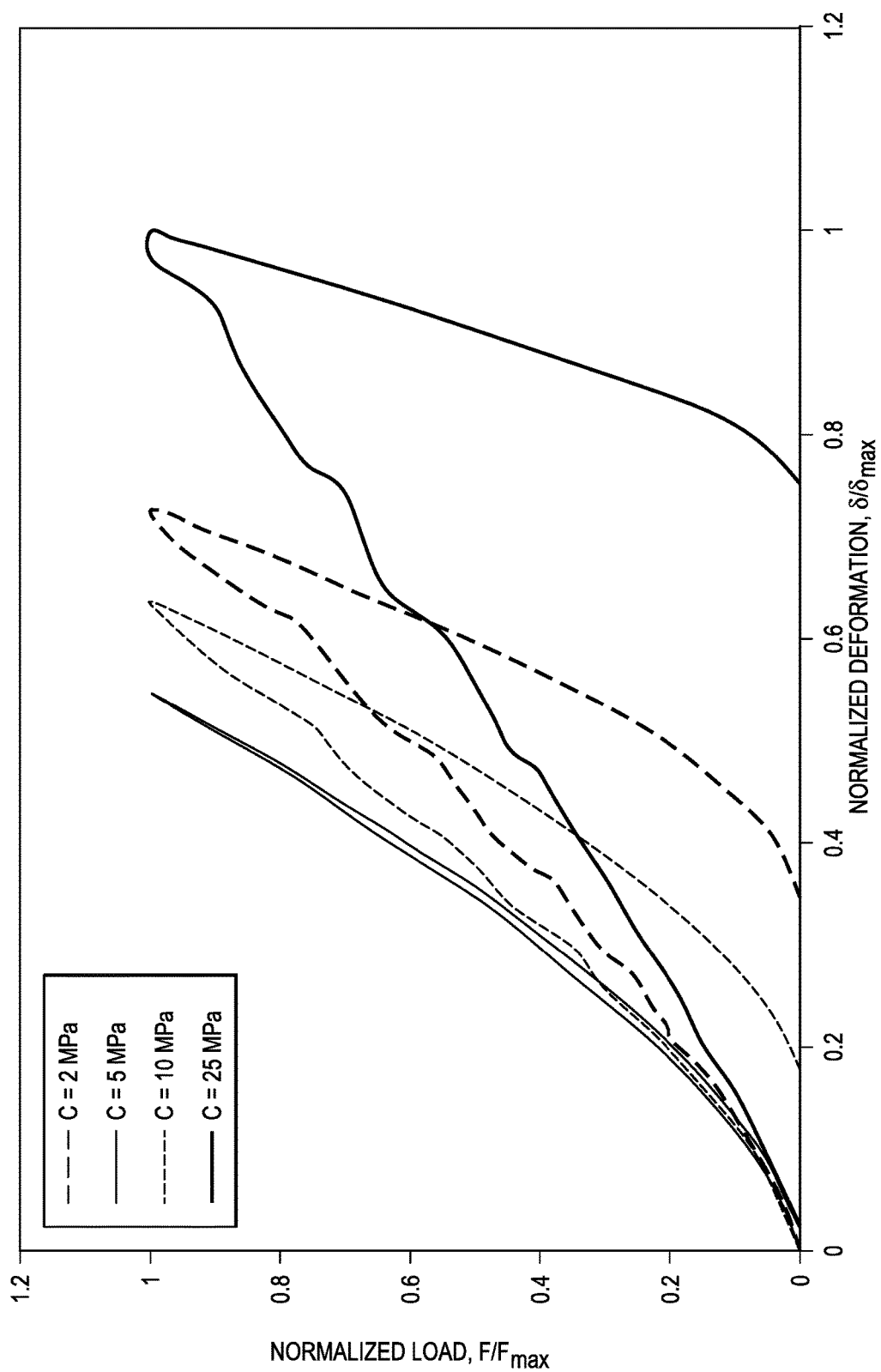
FIG. 8A shows the effect of adjusting cohesive strength on the force-displacement curves in the numerical model.
Figure 8B:
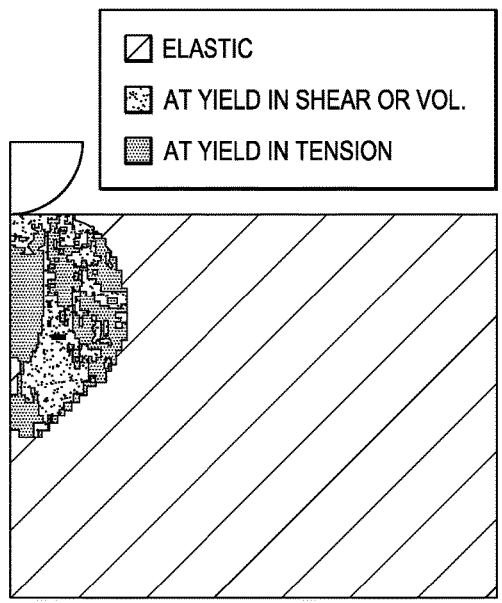
FIGS. 8B-8E shows the extensions and shapes of plastic region at the end of a numerical simulation adjusting cohesive strength.

In another set of numerical tests, an indentation by the simulated indenter into the simulated sample is simulated at same maximum load but different cohesive strengths: 2, 5, 10, and 20 MPa. FIG. 8A shows the influence of cohesive strength on the force-displacement curves in the indentation test. In all the simulations, the maximum load is same (500 KN); the tensile strength is set to a high value so the tensile yielding is prevented. The extensions and shapes of plastic region at the end of the simulation are displayed in FIGS. 8B-8E.

Figure 8C:
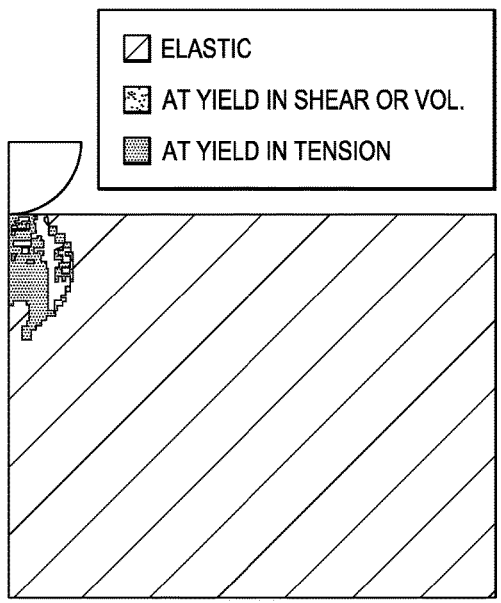
Figure 8D:
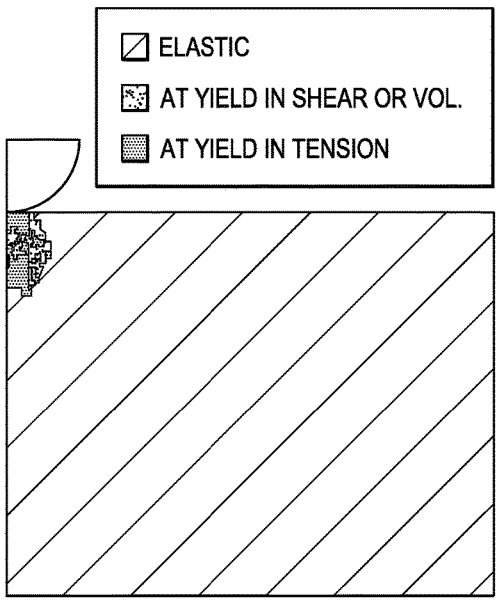
Figure 8E:
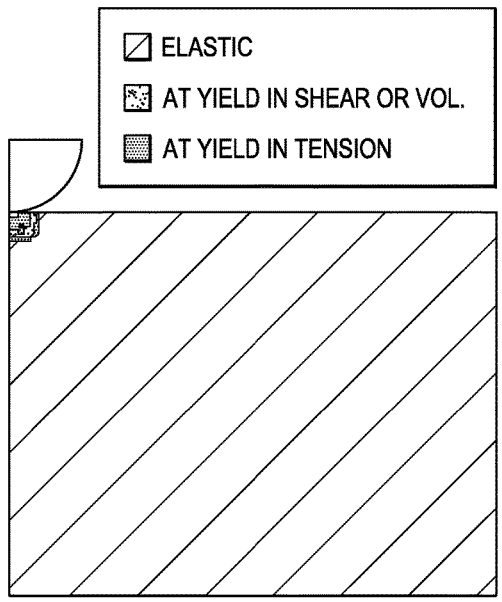
Figure 8F:
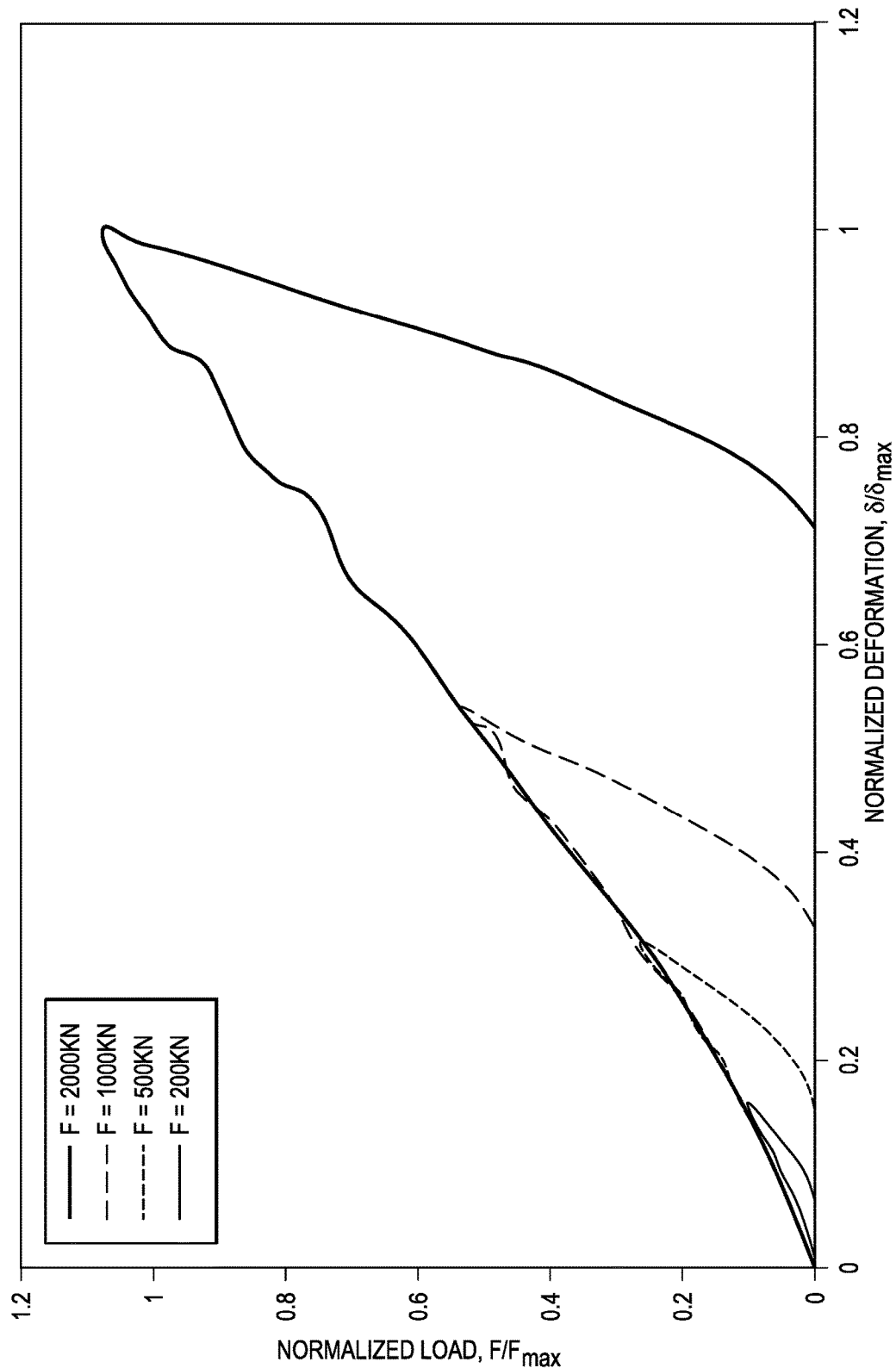
FIG. 8F shows the effect of adjusting maximum load while maintaining the same cohesive strength on the force-displacement curves in the numerical model.

In FIG. 8F, all the indentation tests are conducted with same cohesive strength (5 MPa) but different maximum loads, that is, the indentation stopped at maximum load of 200, 500, 1000 and 2000 KN. For comparison purpose, the loads and deformations in the plot are normalized by the maximum deformation and load in the run with 2000 KN. The shapes of loading-unloading curves are self-similar at different level of loads.

Figure 9A:
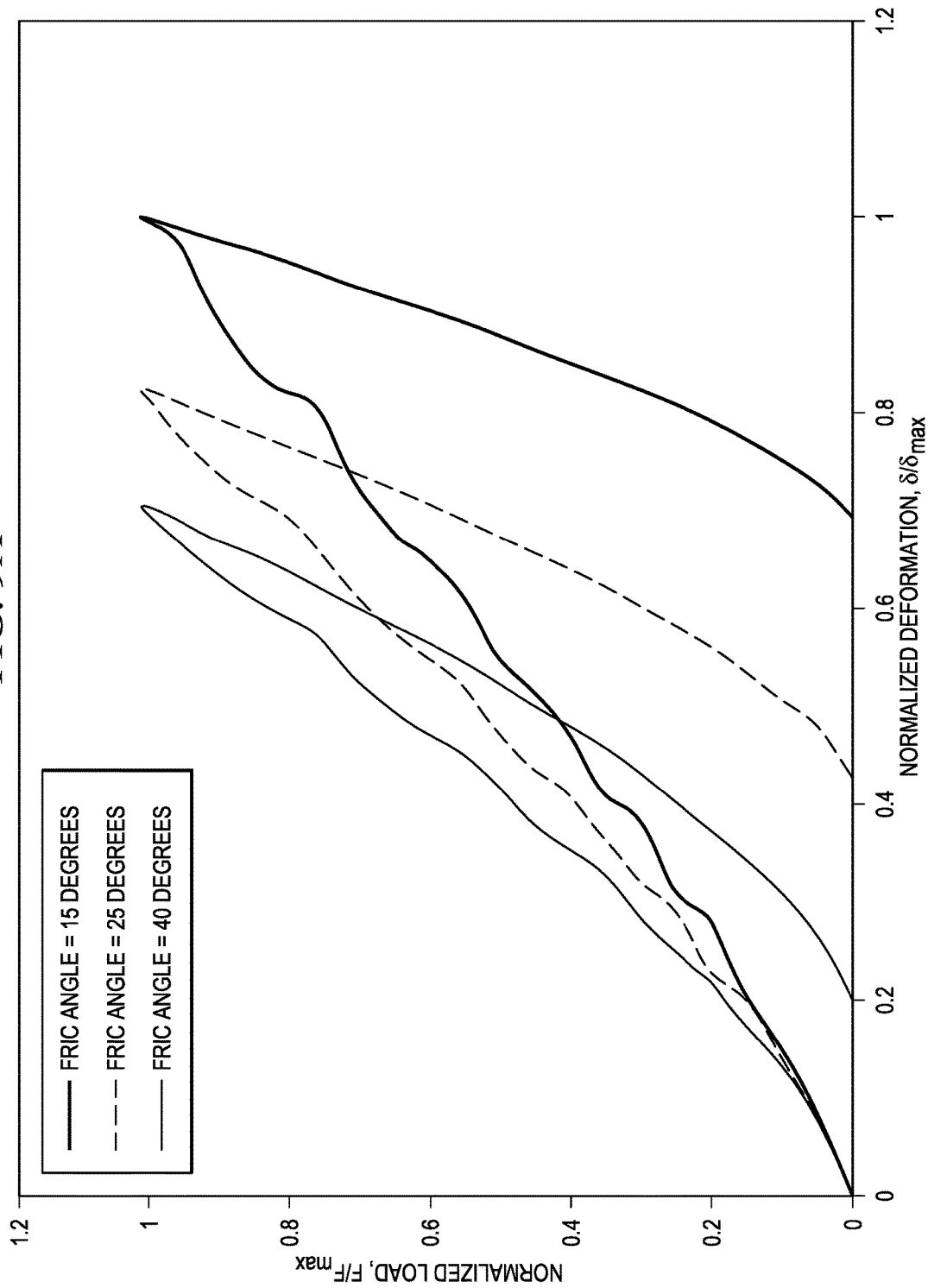
FIG. 9A shows the effect of adjusting internal friction angle on the force-displacement curves in the numerical model.
Figure 9B:
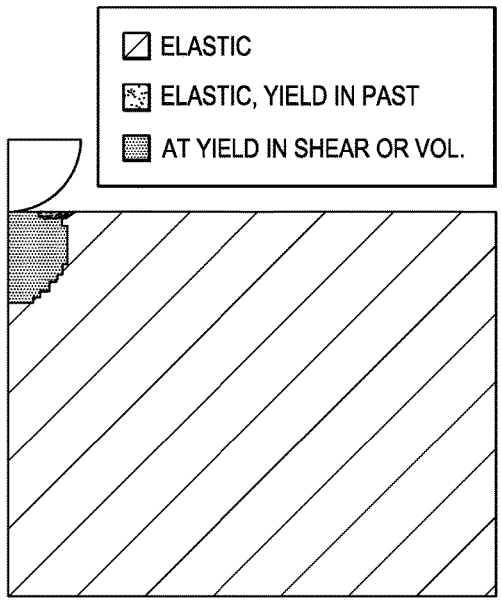
FIGS. 9B-9D shows the extensions and shapes of plastic region at the end of a numerical simulation adjusting internal friction angle.
Figure 9C:
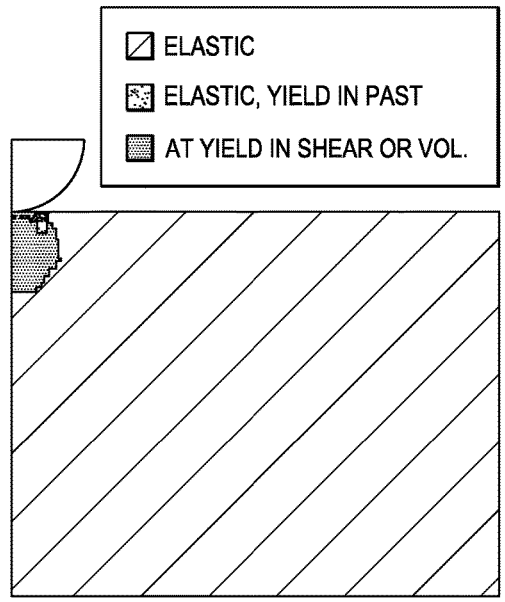
Figure 9D:
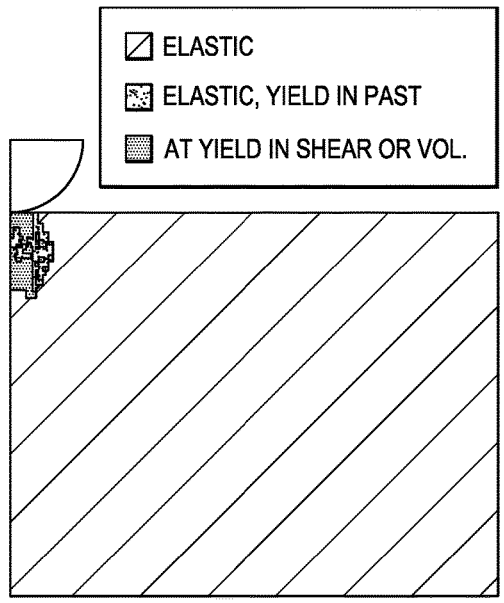

Besides cohesive strength, internal frictional angle is another important property that affects shear yielding. The indentation process is simulated for frictional angle of 15°, 25° and 40° within the simulated sample with cohesive strength of 10 MPa and tensile yielding suppressed. The force-deformation curves recorded in the models are provided in FIG. 9A. The sensitivity of force-deformation curves to frictional angle is similar to the observations on cohesive strength. The plastic regions in these three cases are shown in FIGS. 9B-9D. The size of plastic regions reduces as frictional angle increases.

Figure 10A:
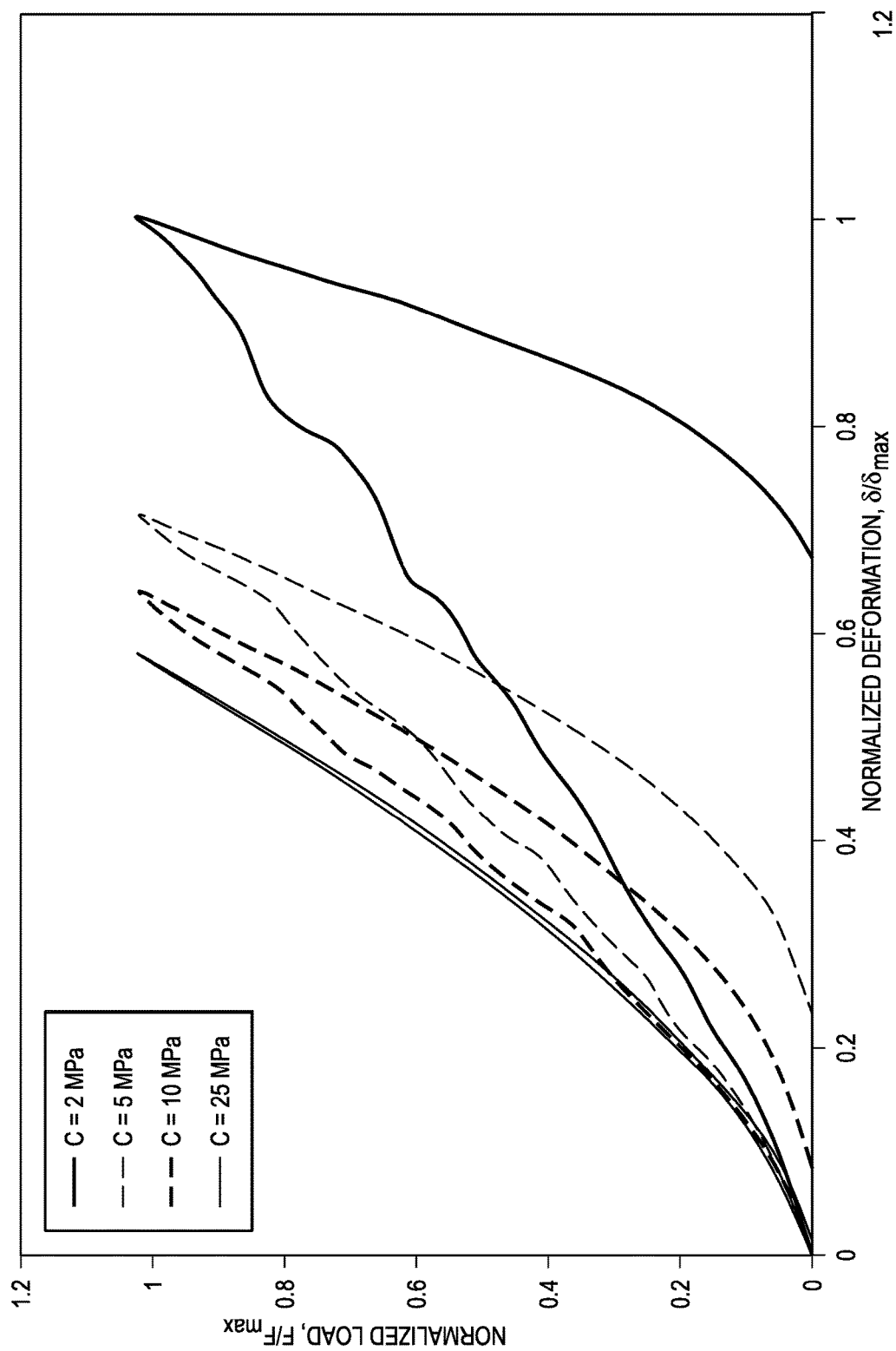
FIG. 10A shows the effect of adjusting cohesive strength on the force-displacement curves in the numerical model.
Figure 10B:
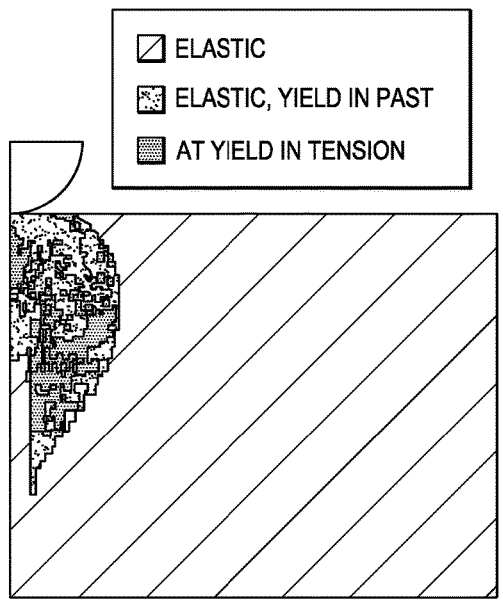
FIGS. 10B-10E shows the extensions and shapes of plastic region at the end of a numerical simulation adjusting cohesive strength.
Figure 10C:
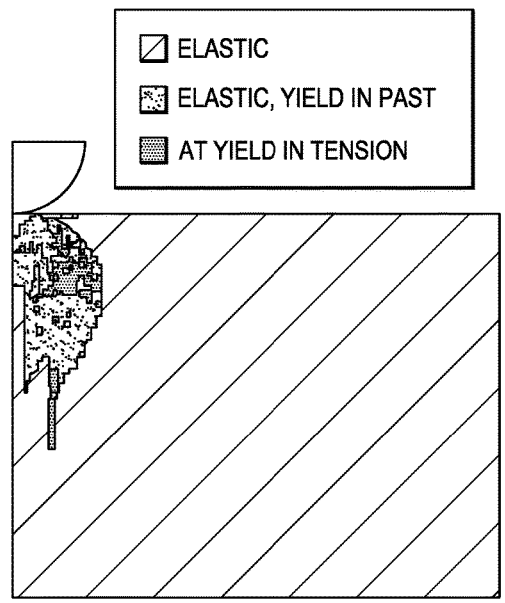
Figure 10D:
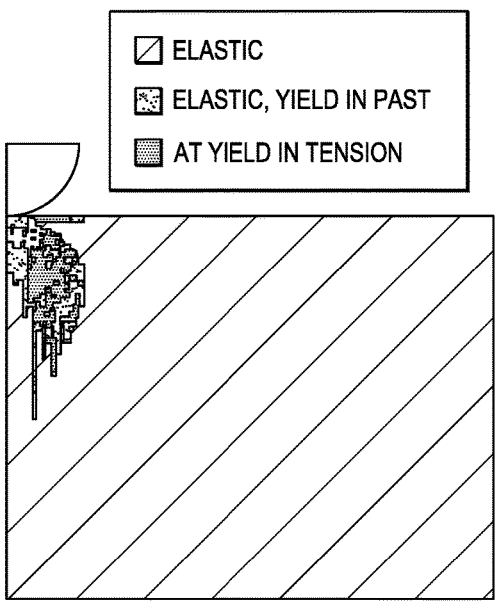
Figure 10E:
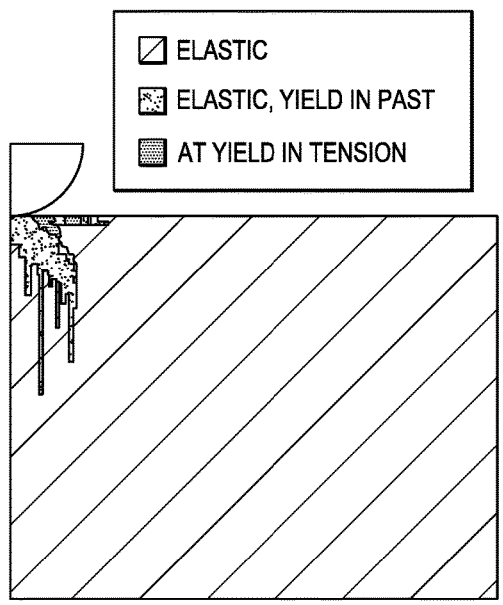
Figure 10F:
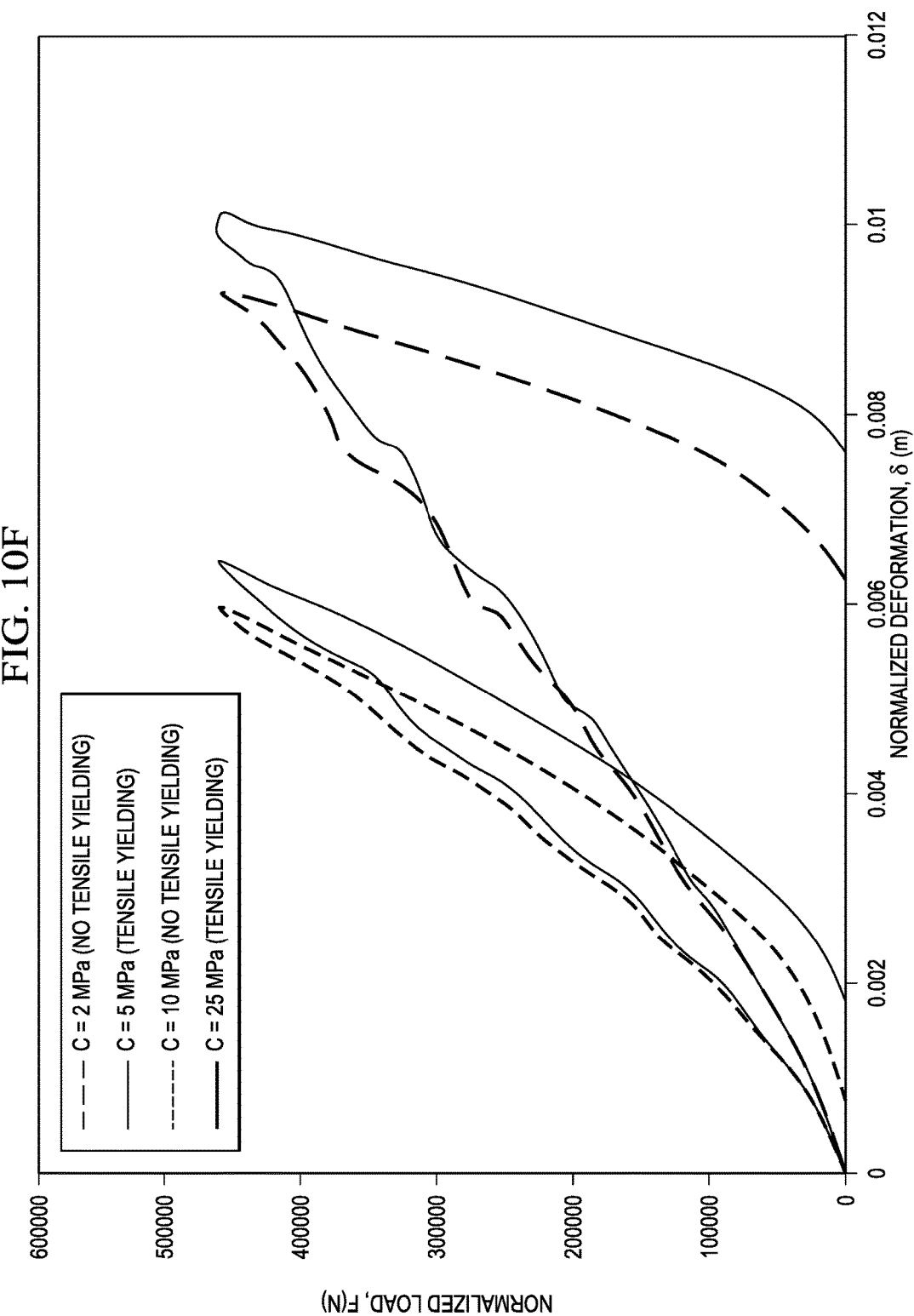
FIG. 10F shows the effect of adjusting cohesive strength on the force-displacement curves while adjusting the tensile strength in the numerical model.
Figure 10G:
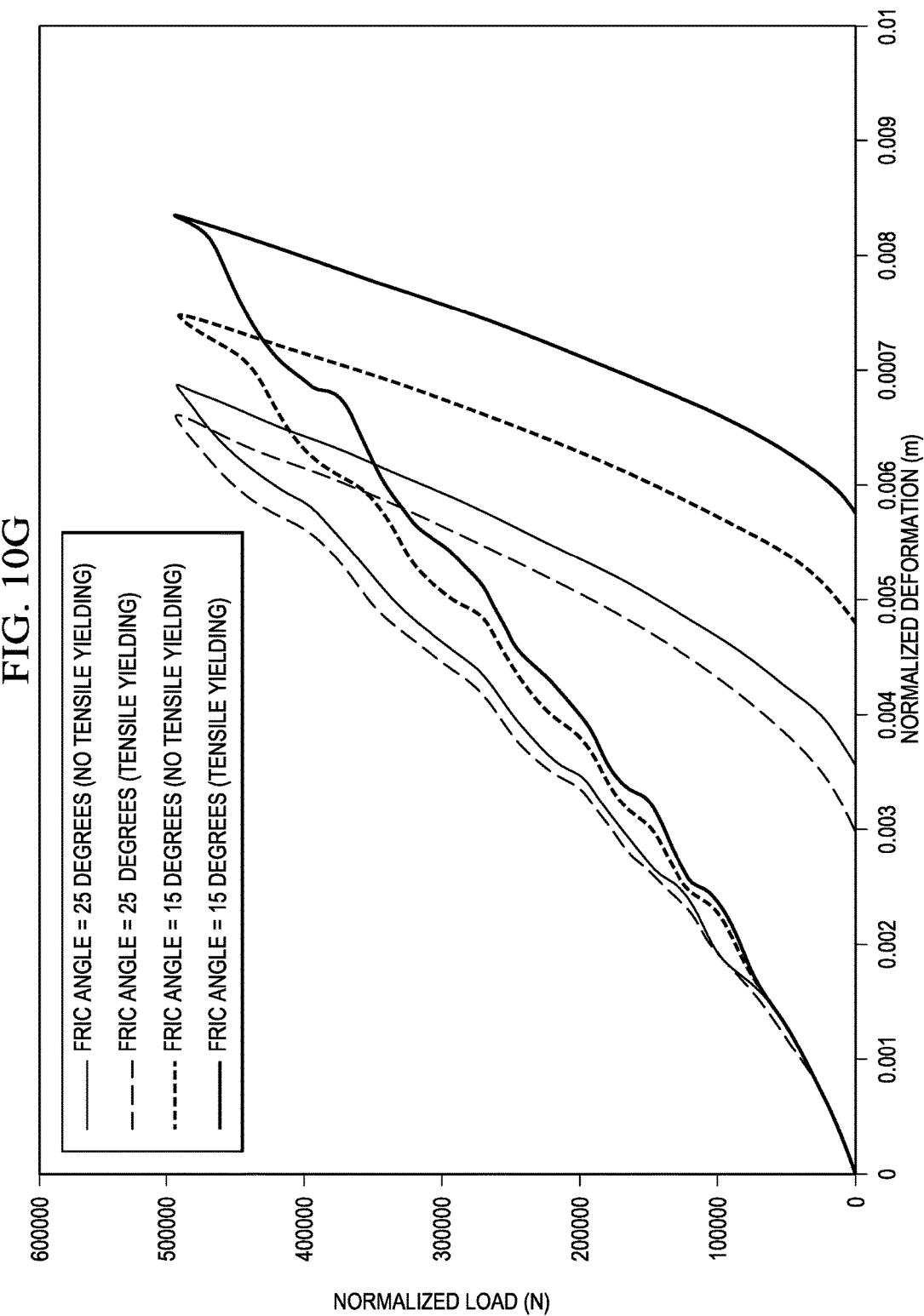
FIG. 10G shows the effect of adjusting friction angle with and without tensile yielding on the force-displacement curves in the numerical model.

Real rocks have limited cohesive strength and tensile strength and they can yield in both shear and tensile modes under many commonly encountered loading conditions. The indentation model is re-run for cohesive strength of 2, 5, 10 and 25 MPa and tensile strength of 1 MPa. Both shear yielding and tensile yielding are observed to take place during the indentation process, as indicated in FIGS. 10B-10E. The recorded force-deformation curves are shown in FIG. 10A. At the first glance, the results look very similar to FIG. 8A where the tensile strength was set to infinity. In FIG. 10F, the force-deformation curves from infinite tensile strength and 1 MPa tensile strength are compared for cohesive strength of 2 and 10 MPa, which indicates that, if combined with shear yielding, tensile yielding has non-negligible effect on the force-deformation curve. This is confirmed by FIG. 10G, which presents the force-deformation curves for another two frictional angles, i.e., 25° and 15°, but with constant cohesive strength of 10 MPa and tensile strength of 1 MPa. The tensile yielding reduces the deformation for the same magnitude of maximum load, this is because tensile yielding absorbs some kinetic energy thus less energy can be spent to break material in shear yielding mode and subsequently the indentation depth is reduced.

Based on the simulation results, for Mohr-Coulomb type materials, the nonsmoothness of the loading portion is introduced by shear yielding and slip, as it is only observed in the simulations with occurrence of shear failure, that is, it does not appear in the simulations of indenting elastic material or elastoplastic materials with only tensile yielding.

A typical force-displacement curve consists of loading, hold and unloading phases, which represents elastoplastic, rheological and elastic mechanical response of the material, respectively. Hardness (H) and reduced Young's modulus ($E^*$) can be extracted from the unloading phase of the force-displacement curve. Hardness is defined as the ratio of the peak load ($P_{max}$) to the projected contact area ($A_c$) at peak load:

$$H = \frac{P_{max}}{A_c} \quad (4)$$

Reduced Young's modulus is calculated from the indenter geometry, the slope of unloading curve and projected area at the peak load:

$$E^* = \frac{1}{\beta} \frac{\sqrt{\pi}}{2} \frac{S}{\sqrt{A_c}} \quad (5)$$

where S is the slope of the unloading curve; $\beta$ is the geometry correction factor of the indentation tip 108: 1 for spherical and cone tips, 1.034 for Berkovich and cubic corner tips, and 1.012 for Vickers and Knoop tips.

The hardness and modulus values tabulated in Table 1 are calculated from the force-displacement curves measured in the simulations with different peak loads displayed in FIG. 8C. The projected contact area was measured in the numerical model at the moment of peak load. The target reduced Young's modulus can be evaluated from the input elastic properties of the indenter and the indented material, which is around 2.8 GPa. The calculation results seem to indicate that the reduced Young's modulus gets overestimated in deep indentations and underestimated in shallow indentations.

TABLE 1

Hardness and modulus calculated from the numerical models

| F (kN) | $A_c$ (cm$^2$) | S (MN/m) | H (MPa) | E* (GPa) |
|---|---|---|---|---|
| 100 | 17.3 | 115.5 | 115.3 | 2.46 |
| 500 | 30.8 | 190.3 | 162.4 | 3.04 |
| 1000 | 57.3 | 256.4 | 174.6 | 3.00 |
| 2000 | 100.6 | 398.0 | 198.7 | 3.52 |

Single-Stage Test

As fine-grained sedimentary geological materials, shales are primarily composed of soft organic, medium stiff clay, and hard minerals such as quartz, feldspar and pyrite. Since quartz, feldspar and pyrite have similar mechanical properties, they can be grouped together as QFP. Each phase has its own distinct mechanical properties. The mechanical properties of a shale sample as composite material will be determined by the volume fractions and distributions of all the phases. As the volume of the shale sample increases, its mechanical properties and behaviors will tend to stabilize. Representative element volume (REV) is the minimum volume shale samples at and above which a sample demonstrates stabilized mechanical response. It was discovered that the REV of shales is in the order of one-tenth to 3 μm for Woodford shale based on instrumented nano-indentation tests. The corresponding peak load is in the order of hundred millinewtons. Considering the abundance of rock cuttings and micron size REV of shales, nano-indentation test is an ideal means to measure mechanical properties for shale formations encountered in oil/gas exploration and production. Material properties can easily be attributed to a sample 106 based upon the curve resulting from a single nano-indentation test.

Figure 14:
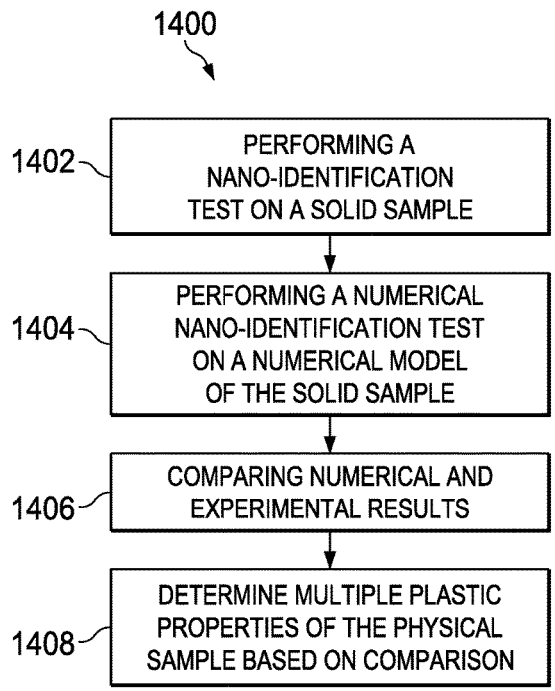
FIG. 14 shows a flowchart of an example of a process for determining plastic properties of a solid sample with a nano-indentation test.

FIG. 14 is a flowchart of an example of a process 1400 for implementing a single-stage nano-indentation test. The single-stage test can be implemented using the nano-indenter tip on a lab sample. At 1402, a nano-indentation is performed on a solid sample. For example, a sample is placed in the nano-indentor 104. While in the sample is in the machine, the nano-indenter tip is pressed onto the sample and the force-displacement curves are recorded. At 1404, the experimentally performed nano-indentation is performed numerically on a numerical model of the experimental sample. At 1406, the numerical and experimental results, for example, respective force-displacement curves, are compared. At 1408, multiple plastic properties of the physical sample are determined based on the comparison.

In some implementations, the single-stage nano-indentation test is done multiple times on different positions of the sample, and the results are averaged. The numerical simulation is similarly done multiple times on positions of the numerical sample that correspond to the physical sample. For each of the experimental measurement and numerical modeling, the resulting force-displacement curves are averaged together to form a single average composite curve which are then compared to each other.

Multi-Stage Test

In the numerical models, material properties are easily tuned to match single-stage lab indentation curves, but it is more difficult to match multistage curves. As the number of stages increase, the matching process becomes more and more difficult but the ranges of the properties are further narrowed down. Therefore, with multistage loading-unloading excursions, the actual material properties can be fully identified. In shallow multistage nano-indentation tests, the mechanical properties of local, single phase material are measured; in deep multistage nano-indentation tests, the averaged mechanical properties of composite shale matrix are measured.

Figure 15:
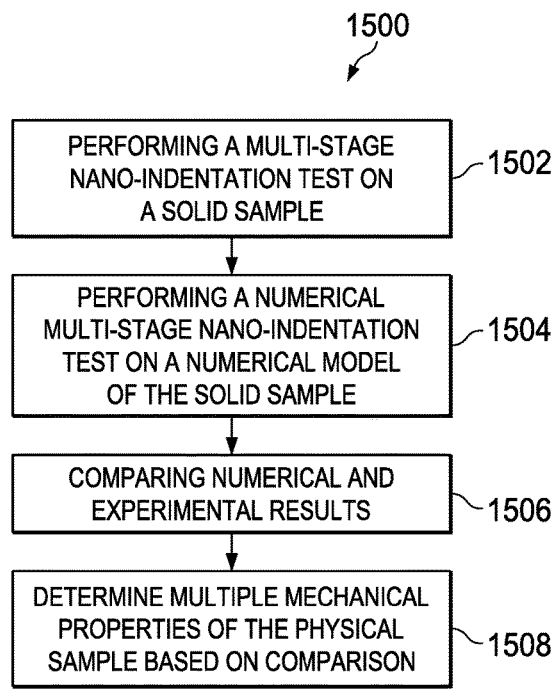
FIG. 15 shows a flowchart of an example of a process for determining a plurality of properties from a multistage nano-indentation test.

FIG. 15 is a flowchart of an example of a process 1500 for implementing a multi-stage nano-indentation test. The multi-stage test can be implemented using the indenter 108 on the lab sample. At 1502, the multi-stage nano-indentation test can be performed on the physical sample. For example, the indentation tip 108 is cycled between multiple loads on the same point on a single sample 106. These test involve indenting a sample 106 with a first load, and unloading the first load to a second load less than the first load. The first load and second load make up the first stage or cycle. In a second stage, the solid sample 106 is indented with a third load greater than the first load, and unloaded to a fourth load less than the third load. In a third stage, the sample 106 is indented with a fifth load greater than the third load, and the fifth load is unloaded to a sixth load less than the fifth load. At 1504, the numerical multi-stage nano-indentation test can be performed on a numerical model of the solid sample. For example, the experimentally performed multi-stage nano-indentation is performed numerically on a numerical model of the experimental sample. At 1506, the numerical and experimental results, for example, respective force-displacement curves, are compared. At 1508, multiple plastic properties of the physical sample are determined based on the comparison. In some implementations, the third load is greater than the second load, fifth load is greater than the fourth load, second load is less than the fourth load, and the fourth load is less than the sixth load.

Example 1

Experimental Test

Figure 11:
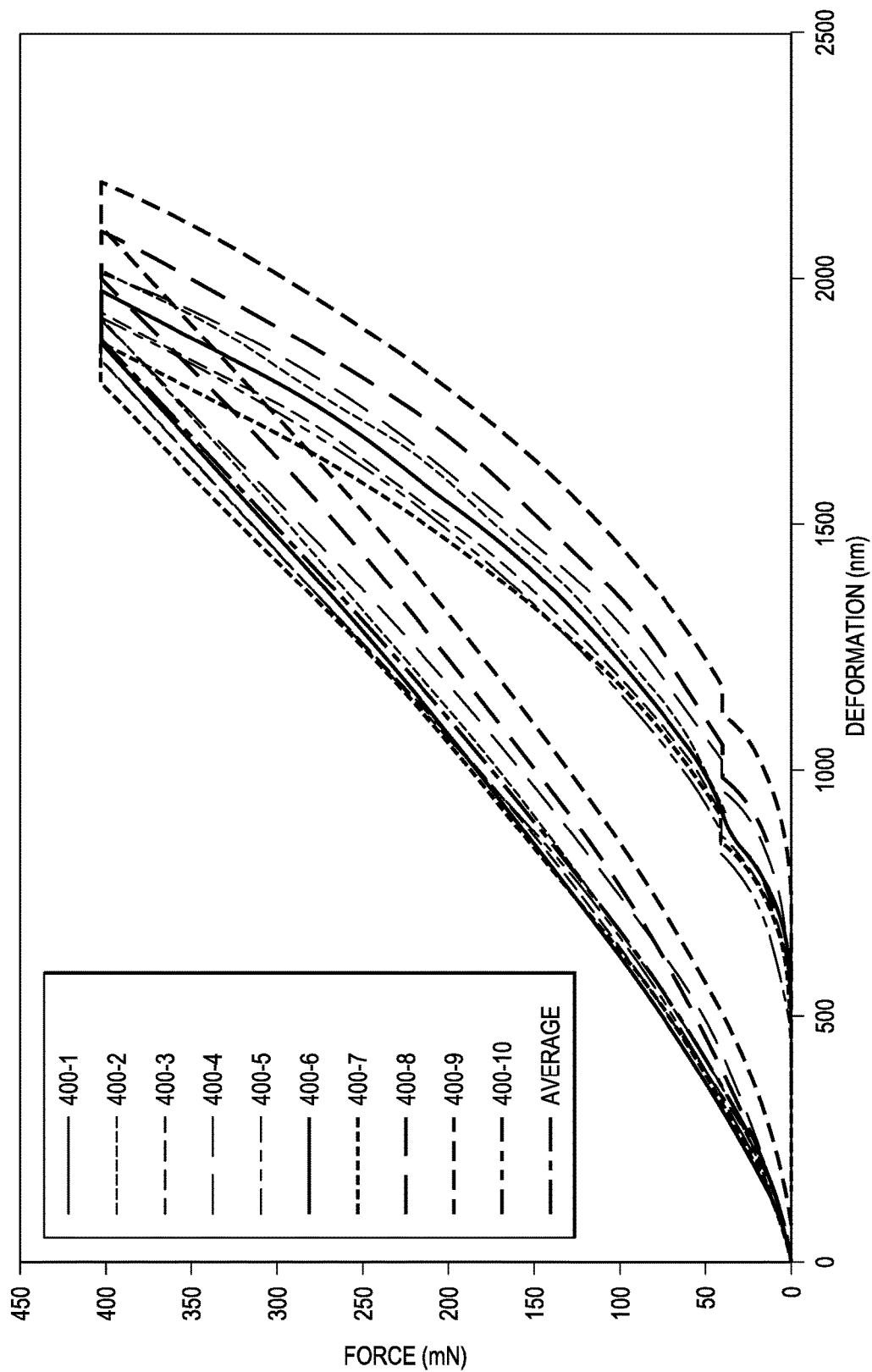
FIG. 11 shows experimental results of ten single indentation tests.

A series of 10 nano-indentation tests were performed on a 10 mm (length)×5 mm (width)×3 mm (thickness) Woodford shale sample 106. The force-displacement curves recorded in the tests are provided in FIG. 11. The peak load is 400 mN and averaged indented depth is nearly 2 μm. The variability is evidently observed in this set of data, which indicates heterogeneous nature of shales.

Numerical Test

Figure 12:
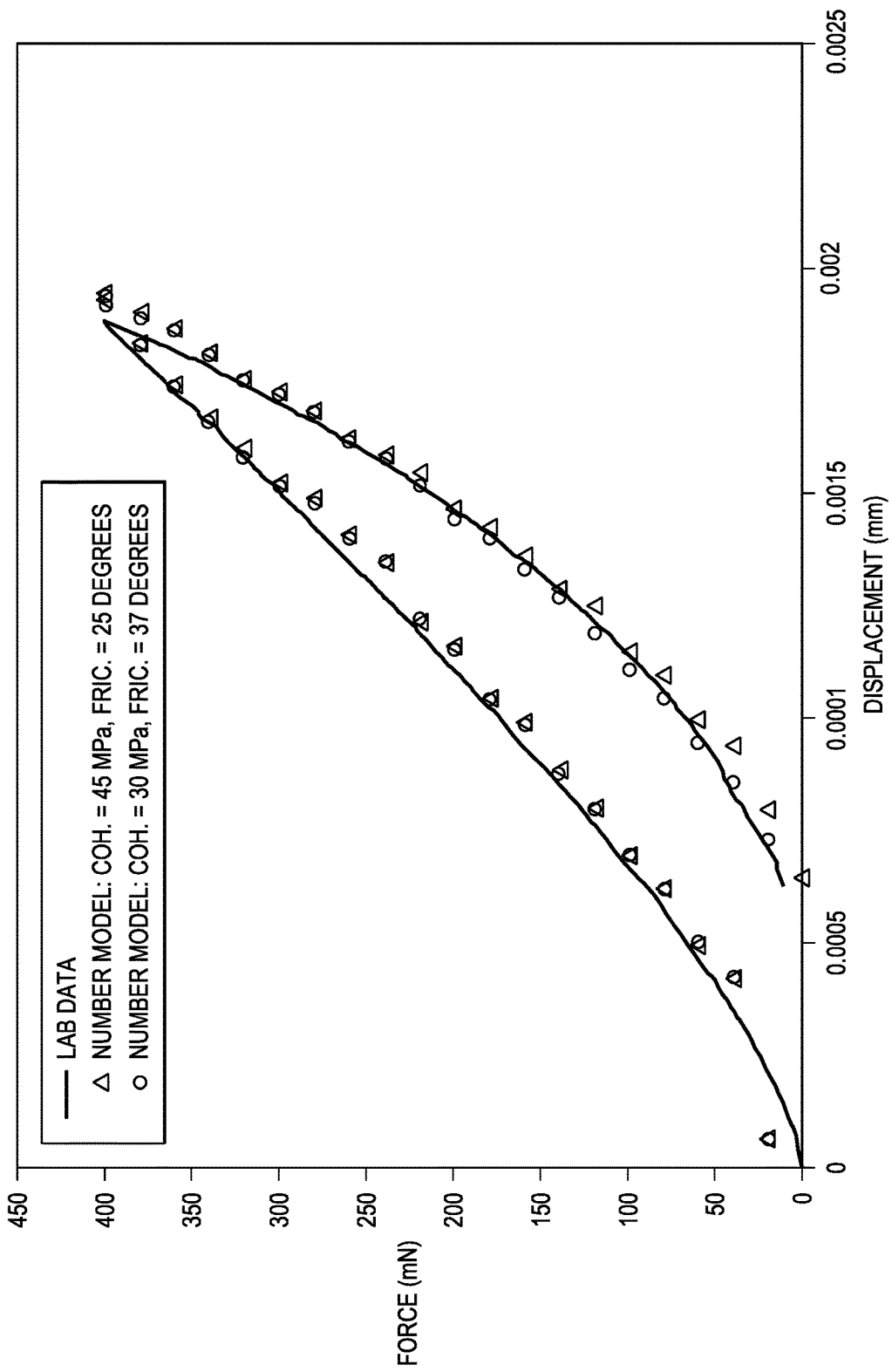
FIG. 12 shows the results of two numerical models in comparison with experimental lab data.

A numerical model was built in FLAC to mimic the lab indentation process. To simplify the simulation, the tensile strength of the simulated sample is set to a high value preventing any tensile yielding. The cohesive strength and frictional angle of the simulated sample are adjusted so that the curve generated by numerical model substantially matched the lab data. After a few arbitrary attempts, cohesion of 45 MPa and frictional angle of 25° gave an acceptable match, as demonstrated by triangular symbol line in FIG. 12. Interestingly, an arbitrary decrease of cohesion to 30 MPa and increase of frictional angle to 37° also gave a similar match, as shown by circular symbol line in FIG. 12. Evidently it is an underdetermined problem to extract multiple properties from a single-stage indentation test. Note, since the creep behavior of the material is not of interest in this study, the hold phase in the force-displacement curve recorded in the lab was removed when comparing with numerical modeling results.

Example 2

Experimental Test

In the three-stage indentation test, the Woodford sample 106 was indented to 100 mN then unloaded to 30 mN (30% of peak load) in the first stage; in the second stage, the indenter was loaded up to 250 mN then unloaded to 75 mN; in the third stage, the indenter was loaded to 400 mN then unloaded to 120 mN.

Numerical Test

Figure 13:
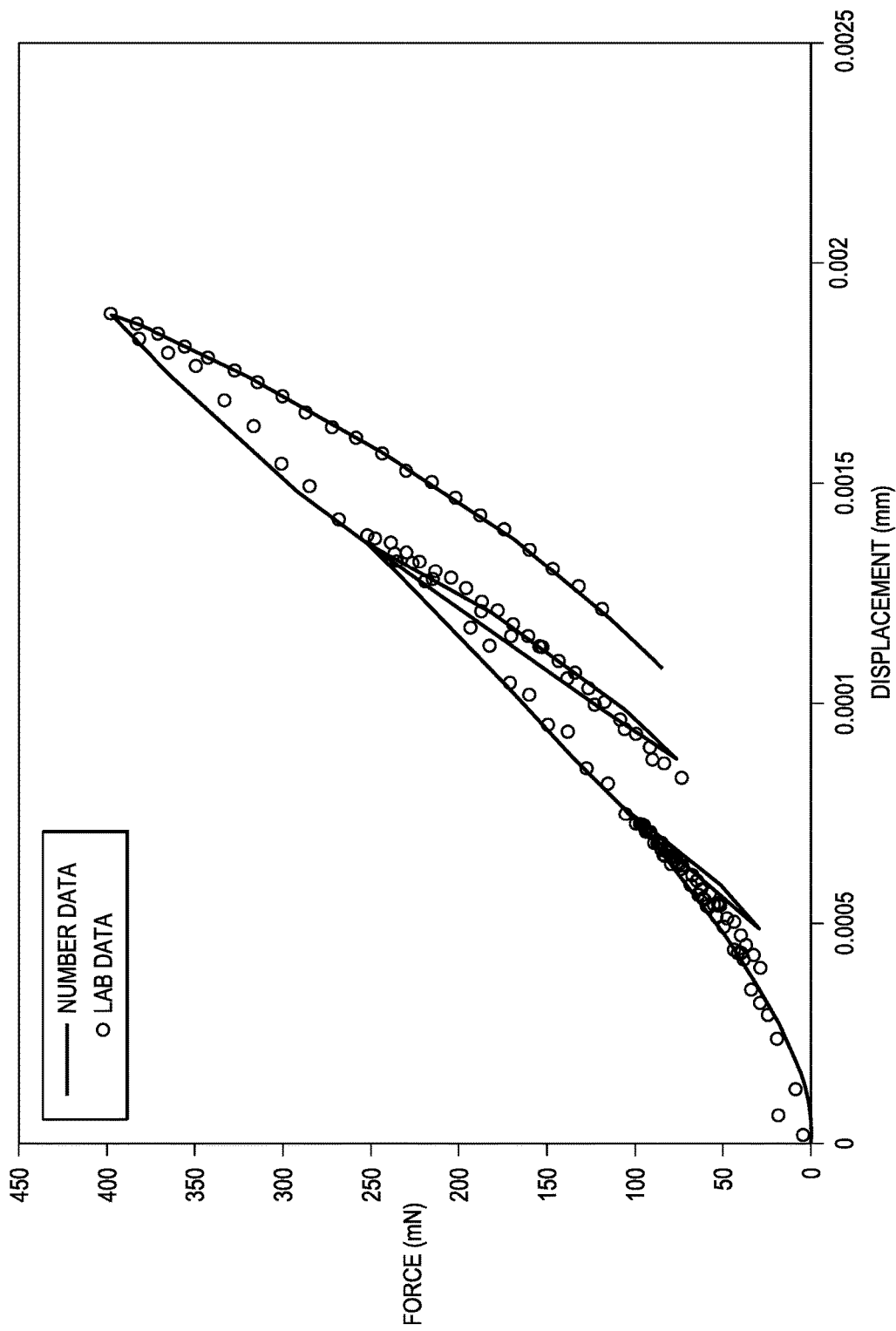
FIG. 13 shows the results of a numerical model in comparison with experimental lab data.

A numerical simulation was performed to match the multistage indentation test in FLAC. With cohesion of 16.5 MPa, friction angle of 40° and tensile strength of 5 MPa, the lab data and numerical modeling results are compared in FIG. 13, in which the line plot is the force-displacement curve recorded in the multistage indentation lab test, the symbol plot is the simulation results generated from numerical models. Note, the match at the load level of 100 mN is not that well because its indentation depth is less than 1 μm, so the curve reflects the response of local material, possibly a single phase; while the indentation depths at load level of 250 mN and 400 mN are deeper than 1 μm at which curve represents the response of composite shale matrix.

Application

The multistage nano-indentation test coupled with numerical modeling is capable of yielding apparent mechanical properties of a geological formation. These properties can be used to determine appropriate drilling mud weights, drilling techniques, and other properties of a wellbore. The tests on one wellbore can be compared with other tests within the same formation to improve the accuracy of reservoir models as well. The results of this technique could potentially be extrapolated to develop a full profile for an entire reservoir.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A method comprising:
performing an experimental multi-stage nano-indentation test on a shale rock sample by:
in a first stage:
indenting, using a nano-indenter, the shale rock sample to a first depth from a surface of the sample, and
withdrawing the nano-indenter to a second depth from the surface of the shale rock sample, the second depth less than the first depth;
in a second stage:
indenting, using the nano-indenter, the shale rock sample to a third depth greater than the first depth, and
withdrawing the nano-indenter to a fourth depth from the surface of the shale rock sample, the fourth depth less than the third depth; and
during the first stage and the second stage, measuring a load on the shale rock sample during the indenting and the withdrawing;
performing a numerical multi-stage nano-indentation test on a numerical model of the shale rock sample, wherein the numerical multi-stage nano-indentation test matches the experimental multi-stage nano-indentation test;
comparing a plurality of experimental force-displacement curves obtained in response to performing the experimental multi-stage nano-indentation test and a plurality of numerical force-displacement curves obtained in response to performing the numerical multi-stage test; and
determining a plurality of mechanical properties of the shale rock sample based on a result of the comparing.

2. The method of claim 1, wherein the shale rock sample is substantially 10 mm long, substantially 5 mm wide and substantially 3 mm thick.

3. The method of claim 1, wherein performing the experimental multi-stage nano-indentation test on the shale rock sample comprises:
in a first stage,
indenting the shale rock sample with a first load, and
unloading the first load to a second load less than the first load; and
in a second stage,
indenting the shale rock sample with a third load greater than the first load, and
unloading the third load to a fourth load less than the third load.

4. The method of claim 3, further comprising:
in a third stage,
indenting the shale rock sample with a fifth load greater than the third load, and
unloading the fifth load to a sixth load less than the fifth load.

5. The method of claim 4, wherein the third load is greater than the second load, wherein the fifth load is greater than the fourth load, wherein the second load is less than the fourth load, and wherein the fourth load is less than the sixth load.

6. The method of claim 4, wherein the first load is about 100 milli-Newtons (mN), the second load is about 30 mN, the third load is about 250 mN, the fourth load is about 120 mN, the fifth load is about 400 mN and the sixth load is about 120 mN.

7. The method of claim 1, further comprising:
in a third stage:
indenting, using the nano-indenter, the shale rock sample to a fifth depth greater than the third depth,
withdrawing the nano-indenter to a sixth depth from the surface of the shale rock sample, the sixth depth less than the fifth depth, and
during the third stage, measuring a load on the shale rock sample during the indenting and the withdrawing.

8. The method of claim 7, wherein a depth to which the nano-indenter indents the surface of the shale rock sample is at most $1/10^{th}$ of a thickness of the shale rock sample.

9. The method of claim 1, wherein performing the numerical multi-stage nano-indentation test on the numerical model of the shale rock sample comprises:
numerically modeling a nano-indenter to perform the experimental nano-scale indentation test on the shale rock sample;
numerically modeling the shale rock sample; and
numerically modeling each stage of the experimental multi-stage nano-indentation test by indenting the numerically modeled shale rock sample with the numerically modeled nano-indenter.

10. The method of claim 9, wherein the shale rock sample is numerically modeled based on mechanical properties of individual components of the shale rock sample.

11. The method of claim 9, wherein the mechanical properties comprise a cohesive strength, a friction angle and a tensile strength.

12. The method of claim 9, wherein the mechanical properties of the individual components based on which the shale rock sample is numerically modeled comprises Young's modulus, Poisson's ratio, cohesive strength, frictional angle and tensile strength.

13. The method of claim 1, wherein comparing the plurality of experimental force-displacement curves obtained in response to performing the experimental multi-stage nano-indentation test and the plurality of numerical force-displacement curves obtained in response to performing the numerical multi-stage test comprises comparing each force-displacement curve obtained in response to performing each experimental stage to each force-displacement curve obtained in response to performing each numerical stage.

14. The method of claim 13, determining a plurality of mechanical properties of the shale rock sample based on a result of the comparing comprises:

determining that the plurality of experimental force-displacement curves match the plurality of numerical force-displacement curves;

identifying mechanical properties of the individual components based on which the shale rock sample was numerically modeled; and determining that the plurality of the mechanical properties of the shale rock sample match the mechanical properties based on which the shale rock sample was numerically modeled.

15. The method of claim 14, wherein determining that the plurality of experimental force-displacement curves match the plurality of numerical force-displacement curves comprises determining that a variance between each experimental force-displacement curve and each corresponding numerical force-displacement curve is less than 5%.

16. The method of claim 1, wherein determining a plurality of mechanical properties of the shale rock sample based on a result of the comparing comprises:

determining that at least one of the plurality of experimental force-displacement curves does not match a corresponding numerical force-displacement curve; and modifying mechanical properties of the individual components based on which the shale rock sample was numerically modeled.

* * * * *